US008080517B2

(12) United States Patent
Bonny

(10) Patent No.: US 8,080,517 B2
(45) Date of Patent: Dec. 20, 2011

(54) CELL-PERMEABLE PEPTIDE INHIBITORS OF THE JNK SIGNAL TRANSDUCTION PATHWAY

(75) Inventor: Christophe Bonny, Lausanne (CH)

(73) Assignee: Xigen SA, Lausanne (CH)

( * ) Notice: Subject to any disclaimer, the term of this patent is extended or adjusted under 35 U.S.C. 154(b) by 0 days.

(21) Appl. No.: 11/224,159

(22) Filed: Sep. 12, 2005

(65) Prior Publication Data
US 2007/0060514 A1    Mar. 15, 2007

(51) Int. Cl.
A61K 38/00 (2006.01)
A61K 38/16 (2006.01)
(52) U.S. Cl. .................. 514/1.1; 514/18.9; 514/21.3
(58) Field of Classification Search .................. None
See application file for complete search history.

(56) References Cited

U.S. PATENT DOCUMENTS

| 4,631,211 A | 12/1986 | Houghten |
| 4,698,327 A | 10/1987 | Nagarajan et al. |
| 4,732,890 A | 3/1988 | Bonelli et al. |
| 5,597,895 A | 1/1997 | Gaynor et al. |
| 5,670,617 A | 9/1997 | Frankel et al. |
| 5,672,479 A | 9/1997 | Johnson et al. |
| 5,674,980 A | 10/1997 | Frankel et al. |
| 5,686,264 A | 11/1997 | Gaynor et al. |
| 5,747,641 A | 5/1998 | Frankel et al. |
| 5,756,684 A | 5/1998 | Johnson et al. |
| 5,804,604 A | 9/1998 | Frankel et al. |
| 5,840,313 A * | 11/1998 | Vahlne et al. ............... 424/208.1 |
| 5,880,261 A | 3/1999 | Waeber et al. |
| 5,989,814 A | 11/1999 | Frankel et al. |
| 5,994,108 A | 11/1999 | Gaynor et al. |
| 5,994,109 A | 11/1999 | Woo et al. |
| 6,043,083 A | 3/2000 | Davis |
| 6,117,632 A | 9/2000 | O'Mahony |
| 6,284,456 B1 | 9/2001 | Jones et al. |
| 6,300,317 B1 | 10/2001 | Szoka, Jr. et al. |
| 6,316,003 B1 | 11/2001 | Frankel et al. |
| 6,348,185 B1 * | 2/2002 | Piwnica-Worms ............ 424/1.69 |
| 6,448,283 B1 | 9/2002 | Ylikoski et al. |
| 6,495,663 B1 | 12/2002 | Rothbard et al. |
| 6,586,403 B1 | 7/2003 | Mathison et al. |
| 6,610,820 B1 * | 8/2003 | Bonny ........................ 530/300 |
| 6,630,351 B1 | 10/2003 | Monahan et al. |
| 6,653,443 B2 | 11/2003 | Zhang et al. |
| 6,740,524 B1 | 5/2004 | Akuta et al. |
| 6,780,970 B2 | 8/2004 | Bonny |
| 6,881,825 B1 | 4/2005 | Robbins et al. |
| 6,960,648 B2 | 11/2005 | Bonny |
| 7,034,109 B2 | 4/2006 | Bonny |
| 2002/0103229 A1 | 8/2002 | Bhagwat et al. |
| 2003/0100549 A1 | 5/2003 | Salituro et al. |
| 2003/0104622 A1 | 6/2003 | Robbins et al. |
| 2003/0108539 A1 | 6/2003 | Bonny |
| 2003/0124113 A1 | 7/2003 | Hillman et al. |
| 2003/0220480 A1 | 11/2003 | Bonny |
| 2004/0082509 A1 | 4/2004 | Bonny |
| 2004/0265879 A1 | 12/2004 | Iversen et al. |
| 2005/0059597 A1 | 3/2005 | Tymianski |
| 2005/0106695 A1 | 5/2005 | Bonny |
| 2006/0223807 A1 * | 10/2006 | Davis et al. .................... 514/248 |
| 2006/0258706 A1 | 11/2006 | Saindane et al. |
| 2006/0270646 A1 | 11/2006 | Graczyk et al. |
| 2007/0003531 A1 | 1/2007 | Mukherji et al. |
| 2008/0008749 A1 | 1/2008 | Pearlman et al. |

FOREIGN PATENT DOCUMENTS

| EP | 0679716 A1 | 11/1995 |
| EP | 0897002 | 2/1999 |
| EP | 1364949 A1 | 11/2003 |
| JP | 58-146538 | 9/1983 |
| JP | 02-221294 | 4/1990 |
| WO | 93/18759 | 9/1993 |
| WO | 94/04562 | 3/1994 |
| WO | 94/05311 | 3/1994 |
| WO | WO 94/04686 | 3/1994 |
| WO | 94/23751 | 10/1994 |
| WO | WO 95/34295 | 12/1995 |
| WO | WO 97/05265 | 2/1997 |
| WO | WO 97/10836 | 3/1997 |
| WO | WO 98/11907 | 3/1998 |
| WO | 98/23781 | 6/1998 |
| WO | WO 98/44106 | 10/1998 |
| WO | WO 98/47913 | 10/1998 |
| WO | 98/49188 | * 11/1998 |
| WO | 98/51325 | 11/1998 |
| WO | 98/51825 | 11/1998 |
| WO | WO 98/52614 | 11/1998 |
| WO | 99/07728 | 2/1999 |
| WO | 99/16787 | 4/1999 |
| WO | 99/50282 | 10/1999 |
| WO | WO 99/49879 | 10/1999 |
| WO | 99/58561 | 11/1999 |
| WO | 99/67284 | 12/1999 |
| WO | 00/12587 | 3/2000 |
| WO | 01/10888 A1 | 2/2001 |
| WO | 01/13957 A2 | 3/2001 |
| WO | 01/15511 A2 | 3/2001 |
| WO | WO 01/27268 | 4/2001 |
| WO | 02/31109 A2 | 4/2002 |
| WO | 02/061105 A2 | 8/2002 |
| WO | 02/062396 A2 | 8/2002 |
| WO | 02/065986 A2 | 8/2002 |
| WO | 02/069930 A1 | 9/2002 |

(Continued)

OTHER PUBLICATIONS

Branden et al., "Introduction to Protein Structure", Garland Publishing Inc., New York, 1991, p. 247.*

(Continued)

Primary Examiner — David J Steadman
(74) Attorney, Agent, or Firm — Morgan, Lewis & Bockius LLP

(57) ABSTRACT

The present invention refers to protein kinase inhibitors and more specifically to inhibitors of the protein kinase c-Jun amino terminal kinase. Additionally, the present invention provides JNK inhibitor sequences, chimeric peptides, nucleic acids encoding same as well as pharmaceutical compositions for treating pathophysiologies associated with JNK signaling.

6 Claims, 7 Drawing Sheets

FOREIGN PATENT DOCUMENTS

| WO | 02/081505 A2 | 10/2002 |
|---|---|---|
| WO | WO 02/081504 | 10/2002 |
| WO | 03/075917 A1 | 9/2003 |
| WO | 03/103698 * | 12/2003 |
| WO | 03/103718 A2 | 12/2003 |
| WO | 2004/022580 A2 | 3/2004 |
| WO | 2004/035793 A1 | 4/2004 |
| WO | 2004/045535 A2 | 6/2004 |
| WO | 2004/054501 A2 | 7/2004 |
| WO | 2004/070052 A2 | 8/2004 |
| WO | 2004/092339 A2 | 10/2004 |
| WO | 2005/084158 A2 | 9/2005 |
| WO | 2005/097116 A1 | 10/2005 |
| WO | 2007/031098 A1 | 3/2007 |
| WO | 2008/028860 A1 | 3/2008 |
| WO | 2009/143864 A1 | 12/2009 |
| WO | 2009/143865 A1 | 12/2009 |

OTHER PUBLICATIONS

Bonny et al., Diabetes 50:77-82, 2001.*
Abaza et al. "Effects of amino acid substitutions outside an antigenic site on protein binding to monoclonal antibodies of predetermined specificity obtained by peptide immunization; demonstration with region 94-100 (antigenic site 3) of myoglobin" J. Protein Chem. 11(5), pp. 433-444 (1992).
Adle-Biassette et al. "Neuronal apoptosis does not correlate with dementia in HIV infection but is related to microglial activation and axonal damage" Neuropathol. Appl. Neurobiol., 25(2);123-133 (1999).
Agrawal et al. "Promiscuous binding nature of SH3 domains to their target proteins", Protein Pept. Lett., 9(3):185-193 (2002).
Barr et al. "Identification of the critical features of a small peptide inhibitor ofJNK activity", J. Biol. Chem. 277(13), pp. 10987-10997 (2002).
Bonny et al. "IB1, a JIP-I-related nuclear protein present in insulin-secreting cells", J. Biol. Chem., 273(4):1843-1846 (1998).
Bonny et al. "Targeting the JNK pathway as a therapeutic protective strategy for nervous system diseases", Rev. Neurosei. 16(1), pp. 57-67 (2005).
Borsello et al. "A peptide inhibitor of c-Jun N-terminal kinase protects against excitotoxicity and cerebral ischemia", Nat Med. 9(9), pp. 1180-1186 (2003).
Borsello et al. "Use of cell-permeable peptides to prevent neuronal degeneration" Trends Mol. Med. 10(5), pp. 239-244 (2004).
Creighton, T. Encyclopedia of Molecular Biology, John Wiley and Sons, Inc. New York, pp. 2027-2033 (1999).
D. Wilson. Preventing Nerve Cell Death in ALS. Internet document <http://www.als.ca/_news/57.aspx~2 pages, Dec. 5, 2001, accessed Aug. 23, 2006.
Database Uniprot Feb. 28, 2003, XP002366175, Retrieved from EBI, Database accession No. Q9WVI9 abstract.
Dickens et al. "A cytoplasmic inhibitor of the JNK signal transduction pathway", Science, 277(5326):693-696 (1997).
EMBL Database Entry, GenBank accession No. AAD20443 (1999).
EMBL Database Entry, GenBank accession No. AAF 32323 (2000).
EMBL Database Entry. GenBank accession No. AF074091 (1999).
EMBL Database Entry, GenBank accession No. AF108959 (1998).
EMBL Database Entry, GenBank accession No. Am22543 (1998).
Fawell et al. "Tat-mediated delivery of heterologous proteins into cells" Proc. Natl. Acad. Sci. USA. 91(2), pp. 664-668 (1994).
GenBank Database Accession No. PH0878, May 1997.
Gotthardt et al. "Interactions of the low density lipoprotein receptor gene family with cytosolic adaptor and scaffold proteins suggest diverse biological functions in cellular communication and signal transduction" J. Biol. Chem. 275(33), pp. 25616-25624 (2000).
Gura et al. "Systems for identifying new drugs are often faulty", Science 278(5340): 1041-1042 (1997).
Heemskerk et al. "From chemical to drug: neurodegeneration drug screening and the ethics of clinical trials", Nat. Neurosci., 5:1027-1029 (2002).
Huq et al. "Specific recognition of HIV-1 TAR RNA by a D-Tat peptide", Nat Struct Biol. 4(11), pp. 881-882 (1997).
Inhibit. Dictionary.com,. The American Heritage @ Stedman's Medical Dictionary. Houghton Mifflin Company. internet document <http://dictionary.reference.com.lbrowseinhibait>, accessed: Oct. 10, 2007, 1 page.
International Search Report for PCT/IB00/01538, dated Aug. 1, 2001.
International Search Report for PCT/IB03/00332, mailing date: Jul. 19, 2004.
International Search Report for PCT/IB03/03094, mailing date: Nov. 13, 2003.
Kennedy et al. "Role of JNK in tumor development", Cell Cycle., 2(3):199-201 (2003).
Kishan et al. "SH3-like fold proteins are structurally conserved and functionally divergent", Curr. Protein Pept. Sci., 6(2):143-150 (2005).
Lee et al. "c-Jun N-terminal kinase (JNK) mediates feedback inhibition of the insulin signaling cascade", J. Biol. Chem., 278(5):2896-2902 (2003).
Li, S. "Specificity and versatility of SH3 and other proline-recognition domains: structural basis and implications for cellular signal transduction", Biochem. J., 390(Pt 3):641-653 (2005).
Mayer et al. "SH3 domains: complexity in moderation", J. Cell Science, vol. 114(7), pp. 1253-1263, 1997.
Mooser et al. "Genomic organization, fine-mapping, and expression of the human islet-brain I (IB1)/c-Jun-amino-terminal kinase interacting protein-1 (JIP-1) gene", Genomics, 55(2):202-208 (1999).
Moulin et al. "Islet-brain (IB)JNK-interacting proteins (JIPs): future targets for the treatment of neurodegenerative diseases?", Curr. Neurovasc. Res., 1(2):111-127 (2004).
Ngo et al. In The Protein Problem and Teritary Structure Prediction, 1994, Merz et al. (ed.), Birkhauser, Boston, MA, pp. 433 and 492-495.
"Parkinson's Disease: Challenges", NIH Publication 05-5595.4/22/05, 22 pages.
Pirvola et al. "Rescue of hearing, auditory hair cells, and neurons by CEP-1347/KT7515, an inhibitor of c-Jun N-terminal kinase activation", J. Neurosci., 20(1):43-50 (2000).
Rickles et al. "Phage display selection of ligand residues important for Src homology 3 domain binding specificity", 92(24): 10909-10913 (1995).
Rudikoff et al. "Single amino acid substitution altering antigen-binding specificity", Proc. Natl. Acad. Sci. USA, 79(6):1979-1983(1982).
Rudinger et al., "Characteristics of the amino acids as components of a peptide hormone sequence", pp. 1-7 (1976).
Schwarze et al. "In vivo protein transduction: delivery of a biologically active protein into the mouse", Science, 285(5433):1569-1572 (1999).
Smilek et al. "A single amino acid change in a myelin basic protein peptide confers the capacity to prevent rather than induce experimental autoimmune encephalomyelitis", Proc. Natl. Acad. Sci. USA, 88(21):9633-9637 (1991).
Tournier et al, "Mitogen-activated protein kinase kinase 7 is an activator of the c-Jun NH2-terminal kinase", Proc. Natl. Acad. Sci. USA. 94(14), pp. 7337-7342 (1997).
Vives et al. "A truncated HIV-1 Tat protein basic domain rapidly translocates through the plasma membrane and accumulates in the cell nucleus", J. Biol. Chem., 272(25):16010-16017 (1997).
Voet et al. Biochemistry, 2nd edition, 235-241 (1995).
W.S. Messer, "Vasopressin and Oxytocin", web document updated Apr. 3, 2000; <http:1/www.neurosci.pharm.utoledo.edu/MBC3320/vasopressin.htm>;5 pages.
Waldmeier et al. "Recent clinical failures in Parkinson's disease with apoptosis inhibitors underline the need for a paradigm shift in drug discovery for neurodegenerative diseases", Biochem. Pharmacol., 72(10): 1197-1206 (2006).
Whitmarsh et al. "Transcription factor AP-1 regulation by mitogen-activated protein kinase signal transduction pathways", J. Mol. Med., 74(10):589-607 (1996).
Yasuda et al. "The JIP group of mitogen-activated protein kinase scaffold proteins", Mol. Cell Biol., 19(10):7245-7254 (1999).
Adler et al., "Regulation of JNK signaling by GSTp", EMBO J. 18(5), pp. 1321-1334 (1999).

Brady et al., "Drug design. Reflections on a peptide", Nature 368, pp. 692-693 (1994).

Brugidou et al., "The Retro-inverso Form of a Homeobox-Derived Short Peptide Is Rapidly Internalized by Cultured Neurons: A New Basis for an Efficient Intracellular Delivery System", Biochem. Biophys. Res. Comm. 214(2), pp. 685-693 (1995).

Chie et al., "Identification of the site of inhibition of oncogenic ras-p21-induced signal transduction by a peptide from a ras effector domain", J Protein Chem. 18(8), pp. 881-884 (1999).

Chorev et al., "A dozen years of retro-inverso peptidomimetics", Acc. Chem. Res. 26, pp. 266-273 (1993).

Chorev et al., "Recent developments in retro peptides and proteins—an ongoing topochemical exploration", Trends Biotechnol. 13(10), pp. 438-445 (1995).

Dang et al., "Nuclear and nucleolar targeting sequences of c-erb-A, c-myb, N-myc, p. 53, HSP70, and HIV tat proteins", J. Biol. Chem. 264(30), pp. 18019-18023 (1989).

Elliott et al., "Intercellular trafficking and protein delivery by a herpesvirus structural protein", Cell, 88(2), pp. 223-233 (1997).

Frankel et al., "Activity of synthetic peptides from the Tat protein of human immunodeficiency virus type 1", Proc. Natl. Acad. Sci. USA, 86, pp. 7397-7401 (1989).

GenBank Accession No. AF218778, Mar. 2006.

Giorello et al., "Inhibition of cancer cell growth and c-Myc transcriptional activity by a c-Myc helix 1-type peptide fused to an internalization sequence", Cancer Res. 58, pp. 3654-3659 (1998).

Guichard et al., "Partially modified retro-inverso pseudopeptides as non-natural ligands for the human class I histocompatibility molecule HLA-A2", J. Med. Chem. 39, pp. 2030-2039 (1996).

Hauber et al., "Mutational analysis of the conserved basic domain of human immunodeficiency virus tat protein", J. Virol. 63(3), pp. 1181-1187 (1989).

Jackson et al., "Heat shock induces the release of fibroblast growth factor 1 from NIH 3T3 cells", Proc. Natl. Aca. Sci. USA, 89, pp. 10691-10695 (1996).

Jameson et al., "A rationally designed CD4 analogue inhibits experimental allergic encephalomyelitis", Nature, 368(6473), pp. 744-746 (1994).

Lebleu, "Delivering information-rich drugs—prospects and challenges", Trends Biotechnol., 14(4), pp. 109-110 (1996).

Lin et al , "Inhibition of nuclear translocation of transcription factor NF-kappa B by a synthetic peptide containing a cell membrane-permeable motif and nuclear localization sequence", J. Biol. Chem. 270, pp. 14255-14258 (1996).

Nagahara et al., "Transduction of full-length TAT fusion proteins into mammalian cells: TAT-p27Kip 1 induces cell migration", Nat Med. 4(12), pp. 1449-1452 (1998).

Noguchi et al., "Regulation of c-Myc through phosphorylation at Ser-62 and Ser-71 by c-Jun N-terminal kinase", J. Biol. Chem. 274(46), pp. 32580-32587 (1999).

Rojas et al., "Controlling epidermal growth factor (EGF)-stimulated Ras activation in intact cells by a cell-permeable peptide mimicking phosphorylated EGF receptor", J. Biol. Chem. 271, pp. 27456-27461 (1996).

Ruben et al., "Structural and functional characterization of human immunodeficiency virus tat protein", J. Virol. 63(1), pp. 1-8 (1989).

Schwarze et al., "In vivo protein transduction: delivery of a biologically active protein into the mouse", Science, 285(5433), pp. 1569-1572 (1999).

Torgerson et al., "Regulation of NF-kappa B, AP-1, NFAT, and STAT1 nuclear import in T lymphocytes by noninvasive delivery of peptide carrying the nuclear localization sequence of NF-kappa B p50", J. Immunol 161(11), pp. 6084-6092 (1998).

Van Regenmortel et al., "D-peptides as immunogens and diagnostic reagents", Curr. Opin. Biotechnol. 9(4), pp. 377-382 (1998).

Vocero-Akbani et al., "Killing HIV-infected cells by transduction with an HIV protease-activated caspase-3 protein", Nat. Med. 5(1), pp. 29-33 (1999).

Yang et al., "Differential targeting of MAP kinases to the ETS-domain transcription factor Elk-1", EMBO J. 7, pp. 1740-1749 (1998).

Zhang et al., "Preparation of functionally active cell-permeable peptides by single-step ligation of two peptide modules", Proc. Natl. Acad. Sci. USA, 95(16), pp. 9184-9189 (1998).

133:204452, 2000, Chemical Abstracs Database, XP002554007.

AAD22543, 2007, GenBank, 2 pages.

Aarts et al., 2002, Science, pp. 846-850.

AF074091, 2007, GenBank, 2 pages.

Aldrian-Herrada et al, 1998, Nucleic Acids Research, pp. 4910-4916.

Assi Kiran et al, 2006, Immunology, pp. 112-121.

Ausubel, 1988, Current Protocols in Molecular Biology, pp. 6.4.01-6.4.10.

Berendsen et al., 1998, Science, pp. 642-643.

Besalle et al., 1990, FEBS Letters, pp. 151-155.

Bonny et al., 1995, Molecular Endrocrinology, pp. 1413-1426.

Bradford et al., 1994, Nature, pp. 744-746.

Bradley et al., 2002, J. Mol. Biol., pp. 373-386.

Branden et al., 1999, Nat. Biotechnol., pp. 784-787.

Lim Jun Man et al, 2003, Journal of Cosmetic Science, pp. 483-491.

Cardozo et al., 2007, Biochimica et Biophysica Acta, pp. 2222-2234.

Chaloin et al., 1998, Biochem. Biophys. Res. Commun., pp. 601-608.

Chemical Approaches to the Synthesis of Peptides and Proteins, pp. 209-236, 1997.

Chemical Approaches to the Synthesis of Peptides and Proteins, pp. 237, 264-267, 1997.

Database WPI, 2010, Thomson Scientific, Table 1, 1-4_ XP002643212.

Derossi et al., 1996, Journal of Biological Chemistry, pp. 18188-18193.

Designing Custom Peptides, 2004, Sigma Genosys, pp. 1-2.

Diabetes (2001), vol. 50, No. supplement 2, ppA294(1217-P).

Dietz et al, 2004, Molecular and Cellular Neurosciences, pp. 85-131.

Dominguez-Bendala et al., 2005, Diabetes, pp. 720-726.

Fornoni et al., 2007, Biochem Biophys Res Comm, pp. 227-233.

Frankel et al., 1988, Cell Press, pp. 1189-1193.

Futaki et al., 2001, Journal of Biological Chemistry, pp. 5836-5840.

Gammon et al, 2003, Bioconjugate Chemistry, pp. 368-376.

Guichard et al., 1994, PNAS, pp. 9765-9769.

Gunaseelan et al, Bioconjugate Chemistry, pp. 1322-1333, 2004.

Hawiger, 1999, Curr. Opin. Chem. Biol., pp. 89-94.

Hayashi et al., 2007, Bioorganic & Medicinal Chemistry Letters, pp. 5129-5132.

Herve et al., 1997, Mol Immunol, pp. 157-163.

Hillier et al, 1995, EMBL Sequence Database, R85141.

Ho et al, 2001, Cancer research, pp. 474-477.

Holinger et al, 1999, Journal of Biological Chemistry, pp. 13298-13304.

Holzberg et al., 2003, Journal of Biological Chemistry, pp. 40213-40223.

Houghten, 1985, PNAS, pp. 5131-5135.

Johnson et al., 2007, Biochmica et Biophysica Acta, pp. 1341-1348.

Kida et al., 2006, Bioorganic & Medicinal Chemistry Letters, pp. 743-745.

Kieber-Emmons et al., 1997, Curr.Opin. Biotechnol., pp. 435-441.

Kisselev, 2002, Structure, pp. 8-9.

Lewis et al, 2003, Journal of Labelled Compounds and Radiopharmaceuticals, pp. S13.

Mann et al, 1991, EMBO, pp. 1733-1739.

Marino et al., 1999, Eur. J. Immunology, 2560-2566.

Marks et al., 1996, JCB, pp. 341-354.

Mazur et al., 1999, J. Biol. Chem., pp. 19655-19660.

Melikov et al., 2005, CMLS Cellular and Molecular Life, pp. 2739-2749.

Mi et al., 2000, Molecular Therapy, pp. 339-347.

Milano Giuseppina et al., 2007, American Journal of Physiology, pp. H1828-H1835.

Mooi et al., 1986, NAR, pp. 2443-2457.

Moon et al., 2008, Cancer Letters, pp. 316-325.

Neundorf et al., 2008, Bioconjugate Chemistry, pp. 1596-1603.

Non et al, 2003, Bioconjugate Chemistry, pp. 44-50.

Non et al, 2005, Advanced Drug Delivery Reviews, pp. 619-628.

Okitsu et al., 2003, Transplant. Proc., p. 479.

Pan Jing et al., 2010, Laboratory Investigation, pp. 156-167.

Penco et al, 2001, Biotechnology and Applied Biochemistry, pp. 151-159.
Peptide Science—Present and Future, pp. 782-787, 805-807, 1999.
Peptide Synthesis Protocols, 1994, pp. 201-239.
Peptide Synthesis Protocols, 1994, pp. 241-247.
Peptides 1996 pp. 447-451, 483-487.
Prantner et. al, 2003, Molecular Imaging Official Journal of the Society for Molecule.
Ramanathan et al, 2001, Pharmaceutical Research, pp. 950-956.
Ribeiro et al., 2003, Biochem. Biophys. Res. Comm., pp. 8769-8881.
Robinson et al., 2005, Bioorganic & Medicinal Chemistry, pp. 2055-2064.
Roy Praveen et al., 2008, World Journal of Gastroenterology, pp. 200-202.
Saito et al., 1997, Molecular Immunology, pp. 1133-1145.
Schimmer et al, 2001, Cell Death and Differentiation, pp. 725-733.
Schinzel et al., 1991, FEBS, pp. 125-128.
Sebestyen et al., 1998, Nat. Biotechnol., pp. 80-85.
Selective Dlmerisation of Cysteines to form Homodimers, 1997, NJE.
Stevens et al., 1998, Eur. J. Immunol, pp. 1272-1279.
Stevens et al., 1998, J. Biol. Chem., pp. 2874-2884.
Torchilin, 2005, Advanced Drug Delivery Reviews, pp. 95-109.
Zoukhri Driss et al., 2006, Journal of Neurochemistry, pp. 126-135.
Wadia et al., 2004, American Pharmaceutical Review 2004 United States, pp. 65-69.
Walsh et al, 2002, Blood, pp. 3439-3448.
Wender et al, 2000, Proceedings of the National Academy of Sciences of the United.
Whitmarsh et al., 1998, Science, pp. 1671-1674.
Wishart et al., 1995, Journal of Biological Chemistry, pp. 26782-26785.
Witkowski et al., 1999, Biochemistry, pp. 11643-11650.
Yamamoto et al., 2002, Current Drug Targets, pp. 123-130.

* cited by examiner

Peptide sequences, Human, Mouse and Rat

```
                    :: **.:
A   IB2     :   IPSPSVEEPHKHRPTTLRL--TTLGAQDS         (SEQ ID NO: 14)
    IB1     :   PGTGCGDTYRPKRPTTLNLFPQVPRSQDT         (SEQ ID NO: 13)
    c-Jun   :   GAYGYSNPKILKQSMTLNLADPVGNLKPH         (SEQ ID NO: 15)
    ATF2    :   TNEDHLAVHKHKHEMTLKFGPARNDSVIV         (SEQ ID NO: 16)

: .*****  *    **;
B   L-IB1(s) :  ---RPKRPTTLNLFPQVPRSQD       (SEQ ID NO: 1)
    L-IB1    :  DTYRPKRPTTLNLFPQVPRSQDT      (SEQ ID NO: 17)
                                °°  °

C   L-TAT       :   NH2-GRKKRRQRRR-COOH                                          (SEQ ID NO: 5)
    L-TAT-IB1(s):   NH2-GRKKRRQRRRPP---RPKRPTTLNLFPQVPRSQD-COOH                   (SEQ ID NO: 9)
    L-TAT-IB1   :   NH2-GRKKRRQRRRPPDTYRPKRPTTLNLFPQVPRSQDT-COOH                  (SEQ ID NO: 23)

D-TAT       :   NH2-RRRQRRKKRG-COOH                                          (SEQ ID NO: 6)
    D-TAT-IB1(s):   NH2---DQSRPVQPFLNLTTPRKER---PPRRRQRRKKRG-COOH                 (SEQ ID NO: 11)
    D-TAT-IB1   :   NH2-TDQSRPVQPFLNLTTPRKPRYTDPPRRRQRRKKRG-COOH                  (SEQ ID NO: 25)
```

Fig. 1

Generic Sequences, Human, Mouse and Rat

| | |
|---|---|
| L-generic-TAT(s) : | NH$_2$-XXXXXRKKRRQRRRXXXX-COOH (SEQ ID NO: 21) |
| L-TAT-IB (generic) (s): | NH$_2$-XXXXXXXXRKKRRQRRRXXXXXRPTTLXLXXXXXQDX-COOH (SEQ ID NO: 10) |
| L-TAT-IB (generic) : | NH$_2$-XXXXXXXXRKKRRQRRRXXXXXRPTTLXLXXXXXQDS/TX-COOH (SEQ ID NO: 24) |
| D-generic-TAT(s) : | NH$_2$-XXXXXRRRQRRKKRXXXX-COOH (SEQ ID NO: 22) |
| D-TAT-IB (generic) (s): | NH$_2$-XDQXXXXXLXLTTPRXXXXXRRRQRRKKRXXXXXXX-COOH (SEQ ID NO: 12) |
| D-TAT-IB (generic) : | NH$_2$-XT/SDQXXXXXLXLTTPRXXXXXXXRRRQRRKKRRXXXXXX-COOH (SEQ ID NO: 26) |

CELL-PERMEABLE PEPTIDE INHIBITORS OF THE JNK SIGNAL TRANSDUCTION PATHWAY

FIELD OF THE INVENTION

The present invention refers to protein kinase inhibitors and more specifically to inhibitors of the protein kinase c-Jun amino terminal kinase. Additionally, the present invention provides JNK inhibitor sequences, chimeric peptides, nucleic acids encoding same as well as pharmaceutical compositions for treating pathophysiologies associated with JNK signaling.

SUMMARY OF THE INVENTION

The present invention is based in part on the discovery of peptides that are effective inhibitors of JNK proteins. The peptides, referred to herein as JNK peptide inhibitors, decrease the downstream cell-proliferative effects of c-Jun amino terminal kinase (JNK).

Accordingly, the invention includes novel JNK inhibitor peptides, as well as chimeric peptides which include a JNK peptide inhibitor linked a trafficking peptide that can be used to direct a peptide on which it is present do a desired cellular location. The trafficking sequence can be used to direct transport of the peptide across the plasma membrane. Alternatively, or in addition, the trafficking peptide can be used to direct the peptide to desired intracellular location, such as the nucleus.

The JNK inhibitor peptides can be present as polymers of L-amino acids. Alternatively, the peptides can be present as polymers of D-amino acids.

Also included in the invention are pharmaceutical compositions that include the JNK-binding peptides, as well as antibodies that specifically recognize the JNK-binding peptides.

The invention also includes a method of inhibiting expression of a JNK kinase in a cell. In another aspect, the invention includes a method of treating a pathophysiology associated with activation of JNK in a cell or cells. For example, the target cells may be, e.g., cultured animal cells, human cells or micro-organisms. Delivery can be carried out in vivo by administering the chimeric peptide to an individual in whom it is to be used for diagnostic, preventative or therapeutic purposes. The target cells may be in vivo cells, i.e., cells composing the organs or tissues of living animals or humans, or microorganisms found in living animals or humans.

Among the advantages provided by the invention is that the JNK inhibitor peptides are small, and can be produced readily in bulk quantities and in high purity. The inhibitor peptides are also resistant to intracellular degradation, and are weakly immunogenic. Accordingly, the peptides are well suited for in vitro and in vivo applications in which inhibition of JNK-expression is desired.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIGS. 1A-C are diagrams showing alignments of conserved JBD domain regions in the indicated transcription factors. JNK inhibitor sequences were identified by inspecting these sequence alignments. The results of this alignment are exemplarily shown in FIGS. 1A-1C. FIG. 1A depicts the region of highest homology between the JBDs of IB 1, IB2, c-Jun and ATF2. Panel B depicts the amino acid sequence of the JBDs of L-IB1(s) and L-IB1 for comparative reasons. Fully conserved residues are indicated by asterisks, while residues changed to Ala in the GFP-JBD$_{23Mut}$ vector are indicated by open circles. FIG. 1 C shows the amino acid sequences of chimeric proteins that include a JNK inhibitor sequence and a trafficking sequence. In the example shown, the trafficking sequence is derived from the human immunodeficiency virus (HIV) TAT polypeptide, and the JNK inhibitor sequence is derived from an IB1(s) polypeptide. Human, mouse, and rat sequences are identical in Panels B and C.

FIG. 2 is a diagram showing sequences of generic TAT-IB fusion peptides from human, mouse and rat.

DETAILED DESCRIPTION

Figure 3:
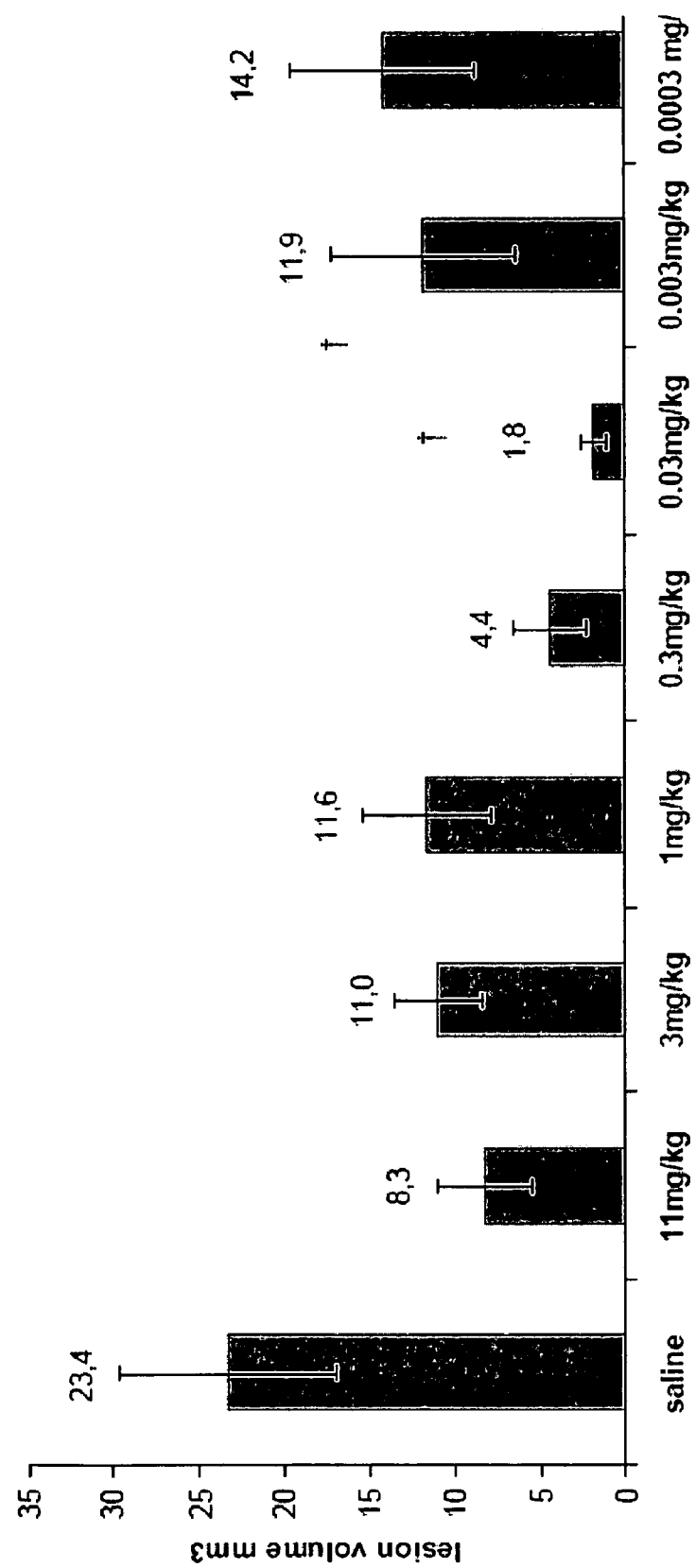
FIG. 3 depicts the results from the evaluation of the neuroprotection against focal cerebral ischemia in a permanent MCAO model. Determination of the efficacy of the protection was carried out at different doses (see FIG. 3). As can be seen from FIG. 3, at least doses of 11 mg/kg, 3 mg/kg, 0.3 mg/kg and 0.03 mg/kg, contribute to a cerebral protection. The best protection is observed at the dose of 0.03 mg/kg.

The c-Jun amino terminal kinase (JNK) is a member of the stress-activated group of mitogen-activated protein (MAP) kinases. These kinases have been implicated in the control of cell growth and differentiation, and, more generally, in the response of cells to environmental stimuli. The JNK signal transduction pathway is activated in response to environmental stress and by the engagement of several classes of cell surface receptors. These receptors can include cytokine receptors, serpentine receptors and receptor tyrosine kinases. In mammalian cells, JNK has been implicated in biological processes such as oncogenic transformation and mediating adaptive responses to environmental stress. JNK has also been associated with modulating immune responses, including maturation and differentiation of immune cells, as well effecting programmed cell death in cells identified for destruction by the immune system. This unique property makes JNK signaling a promising target for developing pharmacological intervention. Among several neurological disorders, JNK signaling is particularly implicated in ischemic stroke and Parkinson's disease.

One approach in combating disorders strongly related to JNK signaling is the provision of inhibitors of the JNK signaling pathway. Such inhibitors as already known in the prior art particularly include e.g. upstream kinase inhibitors (for example, CEP-1347), small chemical inhibitors of JNK (SP600125 and AS601245), which directly affect kinase activity e.g. by competing with the ATP-binding site of the protein kinase, and peptide inhibitors of the interaction between JNK and its substrates (D-JNKI and I-JIP) (see e.g. Kuan et al., Current Drug Targets—CNS & Neurological Disorders, February 2005, vol. 4, no. 1, pp. 63-67(5)).

The upstream kinase inhibitor CEP-1347 (KT7515) is a semisynthetic inhibitor of the mixed lineage kinase family. CEP-1347 (KT7515) promotes neuronal survival at dosages that inhibit activation of the c-Jun amino-terminal kinases (JNKs) in primary embryonic cultures and differentiated PC12 cells after trophic withdrawal and in mice treated with 1-methyl-4-phenyl tetrahydropyridine. Further, CEP-1347 (KT7515) can promote long term-survival of cultured chick embryonic dorsal root ganglion, sympathetic, ciliary and motor neurons (see e.g. *Borasio* et al., Neuroreport. 9(7): 1435-1439, May 11, 1998.).

The small chemical JNK inhibitor SP600125 was found to reduce the levels of c-Jun phosphorylation, to protect dopaminergic neurons from apoptosis, and to partly restore the level of dopamine in MPTP-induced PD in C57BL/6N mice (Wang et al., Neurosci Res. 2004 February; 48(2); 195-202). These results furthermore indicate that JNK pathway is the major mediator of the neurotoxic effects of MPTP in vivo and inhibiting JNK activity may represent a new and effective strategy to treat PD.

A further example of small chemical inhibitors is the aforementioned JNK-Inhibitor AS601245. AS601245 inhibits the JNK signalling pathway and promotes cell survival after cerebral ischemia. In vivo, AS601245 provided significant protection against the delayed loss of hippocampal CA1 neurons in a gerbil model of transient global ischemia. This effect is mediated by JNK inhibition and therefore by c-Jun expression and phosphorylation (see e.g. Carboni et al., J Pharmacol Exp Ther. 2004 July; 310(1):25-32. Epub 2004 Feb. 26).

SUMMARY

A third class of inhibitors of the JNK signaling pathway represent peptide inhibitors of the interaction between JNK and its substrates, as mentioned above. As a starting point for construction of such JNK inhibitor peptides a sequence alignment of naturally occurring JNK proteins may be used. Typically, these proteins comprise JNK binding domains (JBDs) and occur in various insulin binding (IB) proteins, such as IB1 or IB2. The results of such an exemplary sequence alignment is e.g. a sequence alignment between the JNK binding domains of IB1 [SEQ ID NO: 13], IB2 [SEQ ID NO: 14], c-Jun [SEQ ID NO: 15] and ATF2 [SEQ ID NO: 16] (see e.g. FIGS. 1A-1C). Such an alignment reveals a partially conserved 8 amino acid sequence (see e.g. FIG. 1A). A comparison of the JBDs of IB1 and IB2 further reveals two blocks of seven and three amino acids that are highly conserved between the two sequences.

Sequences constructed on basis of such an alignment are e.g. disclosed in WO 01/27268. Particularly, WO 01/27268 discloses small cell permeable fusion peptides, comprising a so-called TAT cell permeation sequence derived from the basic trafficking sequence of the HIV-TAT protein and a minimum 20 amino acid inhibitory sequence of IB1. Both components are covalently linked to each other. Exemplary (and at present the only) inhibitors of the MAPK-JNK signaling pathway disclosed in WO 01/27268, are e.g. L-JNKI1 (JNK-inhibitor peptide composed of L amino acids) or the protease resistant D-JNKI1 peptides (JNK-inhibitor peptide composed of non-native D amino acids). These JNK-inhibitor (JNKI) peptides are specific for JNK (JNK1, JNK2 and JNK3). In contrast to those small compound inhibitors as discussed above, the inhibitor sequences in WO 01/27268, e.g. JNKI1, rather inhibit the interaction between JNK and its substrate. By its trafficking sequence derived from TAT, the fusion peptide is efficiently transported into cells. Due to the novel properties obtained by the trafficking component the fusion peptides are actively transported into cells, where they remain effective until proteolytic degradation.

However, peptides according to WO 01/27268 are still easily accessible by phosphorylases (kinases). Any amino acid of a peptide serving as a target for kinases and, therefore, may be subjected to phosphorylation, represents an important factor for inactivating such peptides. Therefore, it is a first object of the present invention to provide novel inhibitor sequences for the JNK signaling pathway, which retain the functional properties of the peptides as disclosed in WO 01/27268 but provide enhanced stability towards phosphorylases (kinases).

Furthermore, inhibitor sequences according to WO 01/27268 require an expensive recovery and purification step, particularly if prepared in large scale amounts (e.g. for industrial production). Thus, it is a second object of the present invention to provide inhibitor sequences which allow easier and more cost efficient production and recovery than those of the state of the art.

These objects are solved by a JNK inhibitor sequence comprising less than 150 amino acids in length, wherein the JNK inhibitor sequence comprises or consists of at least one amino acid sequence according to SEQ ID NOs: 1, 2, 3 or 4, or a variant, fragment or derivative thereof.

Preferably, the inventive JNK inhibitor sequence binds JNK and/or inhibits the activation of at least one JNK activated transcription factor, e.g. c-Jun or ATF2 (see e.g. SEQ ID NOs: 15 and 16, respectively) or Elk 1.

Typically, JNK inhibitor sequences according to the present invention comprise a total length of less than 150 amino acid residues, preferably a range of 5 to 150 amino acid residues, more preferably 10 to 100 amino acid residues, even more preferably 10 to 75 amino acid residues and most preferably a range of 15 to 50 amino acid residues.

The inventive JNK inhibitor sequence preferably contains or consists of at least one amino acid sequence according to SEQ ID NOs: 1, 2, 3 or 4, or a fragment, derivative or variant thereof More preferably, the inventive JNK inhibitor sequence may contain 1, 2, 3, 4 or even more copies of an amino acid sequence according to SEQ ID NOs: 1, 2, 3 or 4, or a variant, fragment or derivative thereof. If present in more than one copy, these inventive amino acid sequences according to SEQ ID NOs: 1, 2, 3 or 4, or variants, fragments, or derivatives thereof may be directly linked with each other without any linker sequence or via a linker sequence comprising 1 to 10, preferably 1 to 5 amino acids. Amino acids forming the linker sequence are preferably selected from glycine or proline as amino acid residues. More preferably, these inventive amino acid sequences according to SEQ ID NOs: 1, 2, 3 or 4, or fragments, variants or derivatives thereof, may be separated by each other by a hinge of two, three or more proline residues.

The inventive JNK inhibitor sequences as defined above may be composed of L-amino acids, D-amino acids, or a combination of both. Preferably, the inventive JNK inhibitor sequences comprise at least 1, preferably at least 3, more preferably at least 6 and even more preferably at least 10 D- and/or L-amino acids, wherein the D- and/or L-amino acids may be arranged in the inventive JNK inhibitor sequences in a blockwise, a non-blockwise or in an alternate manner.

According to one preferred embodiment the inventive JNK inhibitor sequences may be exclusively composed of L-amino acids. The inventive JNK inhibitor sequences may then comprise or consist of at least one "native JNK inhibitor sequence" according to SEQ ID NO: 1 or 3. In this context, the term "native" or "native JNK inhibitor sequence(s)" is referred to non-altered inventive JNK inhibitor sequences according to any of SEQ ID NOs: 1 or 3, entirely composed of L-amino acids.

Accordingly, the inventive JNK inhibitor sequence may comprise or consist of at least one (native) amino acid sequence $NH_2$—$X_n^b$—$X_n^a$-RPTTLXLXXXXXXXQD-$X_n^b$-COOH [SEQ ID NO: 3]. As used in this context, each X represents an amino acid residue, preferably selected from any (native) amino acid residue. $X_n^a$ represents one amino acid residue, preferably selected from any amino acid residue except serine or threonine, wherein n is 0 or 1. Furthermore, each $X_n^b$ may be selected from any amino acid residue, wherein n is 0-5, 5-10, 10-15, 15-20, 20-30 or more, provided that if n is 0 for $X_n^a$, $X_n^b$ must not comprise a serine or threonine at its C-terminus, in order to avoid a serine or threonine at this position. Preferably, $X_n^b$ represents a contiguous stretch of peptide residues derived from SEQ ID NO: 1 or 3. More preferably, the inventive JNK inhibitor sequence further may comprise or consist of at least one (native) amino acid sequence $NH_2$-RPKRPTTLNLFPQVPRSQD-COOH [SEQ ID NO: 1]. $X_n^a$ and $X_n^b$ represent either D or L amino acids.

According to another preferred embodiment the inventive JNK inhibitor sequences may be composed in part or exclusively of D-amino acids. More preferably, these inventive JNK inhibitor sequences composed of D-amino acids are non-native D retro-inverso sequences of the above (native) JNK inhibitor sequences. The term "retro-inverso sequences" refers to an isomer of a linear peptide sequence in which the direction of the sequence is reversed and the chirality of each amino acid residue is inverted (see e.g. Jameson et al., Nature, 368, 744-746 (1994); Brady et al., Nature, 368, 692-693 (1994)). The advantage of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence or peptide according to the present invention may be converted into an D retro-inverso sequence or peptide by synthesizing a reverse of the sequence or peptide for the corresponding native L-amino acid sequence or peptide.

The inventive D retro-inverso sequences as defined above have a variety of useful properties. For example, inventive D retro-inverso sequences enter cells as efficiently as L-amino acid sequences according to the present invention, whereas the inventive D retro-inverso sequences are more stable than the corresponding L-amino acid sequences.

Accordingly, the inventive JNK inhibitor sequences may comprise or consist of at least one D retro-inverso sequence according to the amino acid sequence $NH_2$—$X_n^b$-DQXXXXXXXXLXLTTPR-$X_n^a$—$X_n^b$-COOH [SEQ ID NO: 4]. As used in this context, X, $X_n^a$ and $X_n^b$ are as defined above (preferably, representing D amino acids), wherein $X_n^b$ preferably represents a contiguous stretch of residues derived from SEQ ID NO: 2 or 4. More preferably, the inventive JNK inhibitor sequences may comprise or consist of at least one D retro-inverso sequence according to the amino acid sequence $NH_2$-DQSRPVQPFLNLTTPRKPR-COOH [SEQ ID NO: 2].

The inventive JNK inhibitor sequences as disclosed above are presented in Table 1 (SEQ ID NO:s 1-4). The table presents the name of the inventive JNK inhibitor sequences, as well as their sequence identifier number, their length, and amino acid sequence. Additionally, prior art sequences according to WO 01/27268 (SEQ ID NOs: 17-26) are also given for comparative reasons. These prior art sequences are not disclosed herein as inventive JNK inhibitor sequences or inventive chimeric peptides and are therefore explicitly excluded from the scope of the present invention by way of a disclaimer.

TABLE 1

| SEQUENCE/ PEPTIDE NAME | SEQ ID NO | AA | SEQUENCE |
|---|---|---|---|
| L-IB1(s) | 1 | 19 | RPKRPTTLNL FPQVPRSQD ($NH_2$-RPKRPTTLNLFPQVPRSQD-COOH) |
| D-IB1(s) | 2 | 19 | DQSRPVQPFL NLTTPRKPR ($NH_2$-DQSRPVQPFLNLTTPRKPR-COOH) |
| L-IB (generic)(s) | 3 | 18 | XRPTTLXLXX XXXXXQDX ($NH_2$-$X_n^b$-$X_n^a$-RPTTLXLXXXXXXXQD-$X_n^b$-COOH) |
| D-IB (generic)(s) | 4 | 18 | XDQXXXXXXX LXLTTPRX ($NH_2$-$X_n^b$-DQXXXXXXXXLXLTTPR-$X_n^a$-$X_n^b$-COOH) |
| L-TAT | 5 | 10 | GRKKRRQRRR ($NH_2$-GRKKRRQRRR-COOH) |

TABLE 1-continued

| SEQUENCE/ PEPTIDE NAME | SEQ ID NO | AA | SEQUENCE |
|---|---|---|---|
| D-TAT | 6 | 10 | RRRQRRKKRG (NH$_2$-RRRQRRKKRG-COOH) |
| L-generic-TAT(s) | 7 | 17 | XXXXRKKRRQ RRRXXXX (NH$_2$-X$_n^b$-RKKRRQRRR-X$_n^b$-COOH) |
| D-generic-TAT(s) | 8 | 17 | XXXXRRRQRR KKRXXXX (NH$_2$-X$_n^b$-RRRQRRKKR-X$_n^b$-COOH) |
| L-TAT-IB1(s) | 9 | 31 | GRKKRRQRRR PPRPKRPTTL NLFPQV PRSQ D (NH$_2$-GRKKRRQRRRPPRPKR PTTLNLFPQVPRSQD-COOH) |
| L-TAT-IB (generic)(s) | 10 | 38 | XXXXXXXRKK RRQRRRXXXX XRPTTL XLXX XXXXXQDX (NH$_2$-X$_n^b$-RKKRR QRRR-X$_n^b$-X$_n^a$-RPTTLXLXXXXXXQ D-X$_n^b$-COOH) |
| D-TAT-IB1(s) | 11 | 31 | DQSRPVQPFL NLTTPRKPRP PRRRQR RKKR G (NH$_2$-DQSRPVQPFLNLTTPR KPRPPRRRQRRKKRG-COOH) |
| D-TAT-IB (generic)(s) | 12 | 38 | XDQXXXXXXX LXLTTPRXXX XXRRRQR RKK RXXXXXXX (NH$_2$-X$_n^b$-DQXXXXX XXLXLTTPR-X$_n^a$-X$_n^b$-RRRQRRKKR-X$_n^b$-COOH) |
| IB1-long | 13 | 29 | PGTGCGDTYR PKRPTTLNLF PQVPRSQ DT |
| 1B2-long | 14 | 27 | IPSPSVEEPH KHRPTTLRLT TLGAQDS |
| c-Jun | 15 | 29 | GAYGYSNPKI LKQSMTLNLA DPVGNLK PH |
| ATF2 | 16 | 29 | TNEDHLAVHK HKHEMTLKFG PARNDSV IV |
| L-IB1 | 17 | 23 | DTYRPKRPTT LNLFPQVPRS QDT |
| D-IB1 | 18 | 23 | TDQSRPVQPF LNLTTPRKPR YTD |
| L-IB (generic) | 19 | 19 | XRPTTLXLXX XXXXXQDS/TX |
| D-IB (generic) | 20 | 19 | XS/TDQXXXXXX XLXLTTPRX |
| L-generic-TAT | 21 | 17 | XXXXRKKRRQ RRRXXXX |
| D-generic-TAT | 22 | 17 | XXXXRRRQRR KKRXXXX |
| L-TAT-IB1 | 23 | 35 | GRKKRRQRRR PPDTYRPKRP TTLNLF PQVP RSQDT |
| L-TAT-IB (generic) | 24 | 42 | XXXXXXXRKK RRQRRRXXXX XXXXRP TTLX LXXXXXXXQD S/TX |
| D-TAT-IB1 | 25 | 35 | TDQSRPVQPF LNLTTPRKPR YTDPPR RRQR RKKRG |
| D-TAT-IB (generic) | 26 | 42 | XT/SDQXXXXXX XLXLTTPRXX XXXX XXRRRQ RRKKRXXXXX XX |

(In Table 1 exemplary sequences as well as their generic formulas are shown for SEQ ID NO's: 1, 2, 5, 6, 9 and 11 and SEQ ID NO's: 3, 4, 7, 8, 10 and 12, respectively).

According to another preferred embodiment, the inventive JNK inhibitor sequence comprises or consists of at least one variant, fragment and/or derivative of the above defined inventive native or non-native amino acid sequences according to SEQ ID NOs: 1, 2, 3 or 4. Preferably, these variants, fragments and/or derivatives retain biological activity of the above disclosed inventive native or non-native JNK inhibitor sequences, particularly of native or non-native amino acid sequences according to SEQ ID NOs: 1, 2, 3 or 4, i.e. binding JNK and/or inhibiting the activation of at least one JNK activated transcription factor, e.g. c-Jun, ATF2 or Elk1. Functionality may be tested by various tests, e.g. binding tests of the peptide to its target molecule or by biophysical methods, e.g. spectroscopy, computer modeling, structural analysis, etc. Particularly, an inventive JNK inhibitor sequence or variants, fragments and/or derivatives thereof may be analyzed by hydrophilicity analysis (see e.g. Hopp and Woods, 1981. Proc Natl Acad Sci USA 78: 3824-3828) that can be utilized to identify the hydrophobic and hydrophilic regions of the peptides, thus aiding in the design of substrates for experimental manipulation, such as in binding experiments, or for antibody synthesis. Secondary structural analysis may also be performed to identify regions of an (inventive) JNK inhibitor sequence or of variants, fragments and/or derivatives thereof that assume specific structural motifs (see e.g. Chou and Fasman, 1974, Biochem 13: 222-223). Manipulation, translation, secondary structure prediction, hydrophilicity and hydrophobicity profiles, open reading frame prediction and plotting, and determination of sequence homologies can be accomplished using computer software programs available in the art. Other methods of structural analysis include, e.g. X-ray crystallography (see e.g. Engstrom, 1974. Biochem Exp Biol 11: 7-13), mass spectroscopy and gas chromatography (see e.g. METHODS IN PROTEIN SCIENCE, 1997, J. Wiley and Sons, New York, N.Y.) and computer modeling (see e.g. Fletterick and Zoller, eds., 1986. Computer Graphics and Molecular Modeling, In: CURRENT COMMUNICATIONS IN MOLECULAR BIOLOGY, Cold Spring Harbor Laboratory Press, Cold Spring Harbor, N.Y.) may also be employed.

Accordingly, the inventive JNK inhibitor sequence may comprise or consist of at least one variant of (native or non-native) amino acid sequences according to SEQ ID NOs: 1, 2, 3 or 4. In the context of the present invention, a "variant of a (native or non-native) amino acid sequence according to SEQ ID NOs: 1, 2, 3 or 4" is preferably a sequence derived from any of the sequences according to SEQ ID NOs: 1, 2, 3 or 4, wherein the variant comprises amino acid alterations of the amino acid sequences according to SEQ ID NOs: 1, 2, 3 or 4. Such alterations typically comprise 1 to 20, preferably 1 to 10 and more preferably 1 to 5 substitutions, additions and/or deletions of amino acids according to SEQ ID NOs: 1, 2, 3 or 4, wherein the variant exhibits a sequence identity with any of the sequences according to SEQ ID NOs: 1, 2, 3 or 4 of at least about 30%, 50%, 70%, 80%, 90%, 95%, 98% or even 99%.

If variants of inventive (native or non-native) amino acid sequences according to SEQ ID NOs: 1, 2, 3 or 4 are obtained by substitution of specific amino acids, such substitutions preferably comprise conservative amino acid substitutions. Conservative amino acid substitutions may include synonymous amino acid residues within a group which have sufficiently similar physicochemical properties, so that a substitution between members of the group will preserve the biological activity of the molecule (see e.g. Grantham, R. (1974), Science 185, 862-864). It is evident to the skilled person that amino acids may also be inserted and/or deleted in the above-defined sequences without altering their function, particularly if the insertions and/or deletions only involve a few amino acids, e.g. less than twenty, and preferably less than ten, and do not remove or displace amino acids which are critical to functional activity. Moreover, substitutions shall be avoided in inventive variants, which lead to additional threonines at amino acid positions which are accessible for a phosphorylase, preferably a kinase, in order to avoid inactivation of the inventive JNK-inhibitor sequence or of the inventive chimeric peptide in vivo or in vitro.

Preferably, synonymous amino acid residues, which are classified into the same groups and are typically exchangeable by conservative amino acid substitutions, are defined in Table 2.

TABLE 2

Preferred Groups of Synonymous Amino Acid Residues

| Amino Acid | Synonymous Residue |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, (Thr), Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, (Thr), Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, (Thr), Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

A specific form of a variant of SEQ ID NOs: 1, 2, 3 or 4 according to the invention is a fragment of the inventive (native or non-native) amino acid sequences according to SEQ ID NOs: 1, 2, 3 or 4", which is typically altered by at least one deletion as compared to SEQ ID NOs 1, 2, 3 or 4. Preferably, a fragment comprises at least 4 contiguous amino acids of any of SEQ ID NOs: 1, 2, 3 or 4, a length typically sufficient to allow for specific recognition of an epitope from any of these sequences. Even more preferably, the fragment comprises 4 to 18, 4 to 15, or most preferably 4 to 10 contiguous amino acids of any of SEQ ID NOs: 1, 2, 3 or 4. Deleted amino acids may occur at any position of SEQ ID NOs: 1, 2, 3 or 4, preferably N- or C-terminally.

Furthermore, a fragment of the inventive (native or non-native) amino acid sequences according to SEQ ID NOs: 1, 2, 3 or 4 may be defined as a sequence sharing a sequence identity with any of the sequences according to SEQ ID NOs: 1, 2, 3 or 4 of at least about 30%, 50%, 70%, 80%, 90%, 95%, 98%, or even 99%.

The inventive JNK inhibitor sequences may further comprise or consist of at least one derivative of (native or non-native) amino acid sequences according to SEQ ID NOs: 1, 2, 3 or 4. In this context, a "derivative of an (native or non-native) amino acid sequence according to SEQ ID NOs: 1, 2, 3 or 4" is preferably an amino acid sequence derived from any of the sequences according to SEQ ID NOs: 1, 2, 3 or 4, wherein the derivative comprises at least one modified L- or D-amino acid (forming non-natural amino acid(s)), preferably 1 to 20, more preferably 1 to 10, and even more preferably 1 to 5 modified L- or D-amino acids. Derivatives of variants or fragments also fall under the scope of the present invention.

"A modified amino acid" in this respect may be any amino acid which is altered e.g. by different glycosylation in various organisms, by phosphorylation or by labeling specific amino acids. Such a label is then typically selected from the group of labels comprising:
   (i) radioactive labels, i.e. radioactive phosphorylation or a radioactive label with sulphur, hydrogen, carbon, nitrogen, etc.;
   (ii) colored dyes (e.g. digoxygenin, etc.);
   (iii) fluorescent groups (e.g. fluorescein, etc.);
   (iv) chemoluminescent groups;
   (v) groups for immobilization on a solid phase (e.g. His-tag, biotin, strep-tag, flag-tag, antibodies, antigen, etc.); and
   (vi) a combination of labels of two or more of the labels mentioned under (i) to (v).

In the above context, an amino acid sequence having a sequence "sharing a sequence identity" of at least, for example, 95% to a query amino acid sequence of the present invention, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted.

For sequences without exact correspondence, a "% identity" of a first sequence may be determined with respect to a second sequence. In general, these two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux et al., 1984, Nucleic Acids Res. 12, 387-395.), for example the programs BEST-FIT and GAP, may be used to determine the % identity between two polynucleotides and the % identity and the % homology between two polypeptide sequences. BESTFIT uses the "local homology" algorithm of (Smith and Waterman (1981), J. Mol. Biol. 147, 195-197.) and finds the best single region of similarity between two sequences. Other programs for determining identity and/or similarity between sequences are also known in the art, for instance the BLAST family of programs (Altschul et al., 1990, J. Mol. Biol. 215, 403-410), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U.S.A 85, 2444-2448.).

JNK-inhibitor sequences according to the present invention may be obtained or produced by methods well-known in the art, e.g. by chemical synthesis or by genetic engineering methods as discussed below. For example, a peptide corresponding to a portion of an inventive JNK inhibitor sequence including a desired region of said JNK inhibitor sequence, or that mediates the desired activity in vitro or in vivo, may be synthesized by use of a peptide synthesizer.

According to a second aspect the present invention provides a chimeric peptide including at least one first domain and at least one second domain, wherein the first domain comprises a trafficking sequence, while the second domain comprises an inventive JNK inhibitor sequence as defined above.

Typically, chimeric peptides according to the present invention have a length of at least 25 amino acid residues, e.g. 25 to 250 amino acid residues, more preferably 25 to 200 amino acid residues, even more preferably 25 to 150 amino acid residues, 25 to 100 and most preferably amino acid 25 to 50 amino acid residues.

As a first domain the inventive chimeric peptide preferably comprises a trafficking sequence, which is typically selected from any sequence of amino acids that directs a peptide (in which it is present) to a desired cellular destination. Thus, the trafficking sequence, as used herein, typically directs the peptide across the plasma membrane, e.g. from outside the cell, through the plasma membrane, and into the cytoplasm. Alternatively, or in addition, the trafficking sequence may direct the peptide to a desired location within the cell, e.g. the nucleus, the ribosome, the endoplasmic reticulum (ER), a lysosome, or peroxisome, by e.g. combining two components (e.g. a component for cell permeability and a component for nuclear location) or by one single component having e.g. properties of cell membrane transport and targeted e.g. intranuclear transport. The trafficking sequence may additionally comprise another component, which is capable of binding a cytoplasmic component or any other component or compartment of the cell (e.g. endoplasmic reticulum, mitochondria, gloom apparatus, lysosomal vesicles). Accordingly, e.g. the trafficking sequence of the first domain and the JNK inhibitor sequence of the second domain may be localized in the cytoplasm or any other compartment of the cell. This allows to determine localization of the chimeric peptide in the cell upon uptake.

Preferably, the trafficking sequence (being included in the first domain of the inventive chimeric peptide) has a length of 5 to 150 amino acid sequences, more preferably a length of 5 to 100 and most preferably a length of from 5 to 50, 5 to 30 or even 5 to 15 amino acids.

More preferably, the trafficking sequence (contained in the first domain of the inventive chimeric peptide) may occur as a continuous amino acid sequence stretch in the first domain. Alternatively, the trafficking sequence in the first domain may be splitted into two or more fragments, wherein all of these fragments resemble the entire trafficking sequence and may be separated from each other by 1 to 10, preferably 1 to 5 amino acids, provided that the trafficking sequence as such retains its carrier properties as disclosed above. These amino acids separating the fragments of the trafficking sequence may e.g. be selected from amino acid sequences differing from the trafficking sequence. Alternatively, the first domain may contain a trafficking sequence composed of more than one component, each component with its own function for the transport of the cargo JNK inhibitor sequence of the second domain to e.g. a specific cell compartment.

The trafficking sequence as defined above may be composed of L-amino acids, D-amino acids, or a combination of both. Preferably, the inventive trafficking sequences comprise at least 1, preferably at least 3, more preferably at least 6 and even more preferably at least 10 L-amino acids and/or D-amino acids, wherein the D- and/or L-amino acids may be arranged in the inventive JNK trafficking sequences in a blockwise, a non-blockwise or in an alternate manner.

According to one alternative embodiment, the trafficking sequence of the inventive chimeric peptide may be exclusively composed of L-amino acids. More preferably, the trafficking sequence of the inventive chimeric peptide comprises or consists of at least one "native" trafficking sequence as defined above. In this context, the term "native" is referred to non-altered trafficking sequences, entirely composed of L-amino acids.

According to another alternative embodiment the trafficking sequence of the inventive chimeric peptide may be exclusively composed of D-amino acids. More preferably, the trafficking sequence of the inventive chimeric peptide may comprise a D retro-inverso peptide of the sequences as presented above.

The trafficking sequence of the first domain of the inventive chimeric peptide may be obtained from naturally occurring sources or can be produced by using genetic engineering techniques or chemical synthesis (see e.g. Sambrook, J., Fritsch, E. F., Maniatis, T. (1989) Molecular cloning: A laboratory manual. 2nd edition. Cold Spring Harbor Laboratory Press, Cold Spring Harbor, N.Y.).

Sources for the trafficking sequence of the first domain may be employed including, e.g. native proteins such as e.g. the TAT protein (e.g. as described in U.S. Pat. Nos. 5,804,604 and 5,674,980, each of these references being incorporated herein by reference), VP22 (described in e.g. WO 97/05265; Elliott and O'Hare, Cell 88: 223-233 (1997)), non-viral proteins (Jackson et al, Proc. Natl. Acad. Sci. USA 89: 10691-10695 (1992)), trafficking sequences derived from Antennapedia (e.g. the antennapedia carrier sequence) or from basic peptides, e.g. peptides having a length of 5 to 15 amino acids, preferably 10 to 12 amino acids and comprising at least 80%, more preferably 85% or even 90% basic amino acids, such as e.g. arginine, lysine and/or histidine. Furthermore, variants, fragments and derivatives of one of the native proteins used as trafficking sequences are disclosed herewith. With regard to variants, fragments and derivatives it is referred to the definition given above for JNK inhibitor sequences. Variants, fragments as well as derivatives are correspondingly defined as set forth above for JNK inhibitor sequences. Particularly, in the context of the trafficking sequence, a variant or fragment or derivative may be defined as a sequence sharing a sequence identity with one of the native proteins used as trafficking sequences as defined above of at least about 30%, 50%, 70%, 80%, 90%, 95%, 98%, or even 99%.

In a preferred embodiment of the inventive chimeric peptide, the trafficking sequence of the first domain comprises or consists of a sequence derived from the human immunodeficiency virus (HIV)1 TAT protein, particularly some or all of the 86 amino acids that make up the TAT protein.

For an inventive trafficking sequence, partial sequences of the full-length TAT protein may be used forming a functionally effective fragment of a TAT protein, i.e. a TAT peptide that includes the region that mediates entry and uptake into cells. As to whether such a sequence is a functionally effective fragment of the TAT protein can be determined using known techniques (see e.g. Franked et al., Proc. Natl. Acad. Sci, USA 86: 7397-7401 (1989)). Thus, the trafficking sequence in the first domain of the inventive chimeric peptide may be derived from a functionally effective fragment or portion of a TAT protein sequence that comprises less than 86 amino acids, and which exhibits uptake into cells, and optionally the uptake into the cell nucleus. More preferably, partial sequences (fragments) of TAT to be used as carrier to mediate permeation of the chimeric peptide across the cell membrane, are intended to comprise the basic region (amino acids 48 to 57 or 49 to 57) of full-length TAT.

According to a more preferred embodiment, the inventive trafficking sequence may comprise or consist of an amino acid sequence containing TAT residues 48-57 or 49 to 57, and most preferably a generic TAT sequence $NH_2$—$X_n^b$-RKKRRQRRR-$X_n^b$-COOH [SEQ ID NO: 7], wherein $X_n^b$ is as defined above. Alternatively, the inventive trafficking sequence may comprise or consist of a peptide containing e.g. the amino acid sequence $NH_2$-GRKKRRQRRR-COOH [SEQ ID NO: 5].

According to another more preferred embodiment the inventive trafficking sequence may comprise a D retro-inverso peptide of the sequences as presented above, i.e. the D retro-inverso sequence of the generic TAT sequence having the sequence $NH_2$—$X_n^b$-RRRQRRKKR-$X_n^b$-COOH [SEQ ID NO: 8]. Also here, $X_n^b$ is as defined above (preferably representing D amino acids). Furthermore, the number of "$X_n^b$" residues in any of SEQ ID NOs:7-8 is not limited to the one depicted, and may vary as described above. Most preferably, the inventive trafficking sequence may comprise the D retro-inverso sequence $NH_2$-RRRQRRKKRG-COOH [SEQ ID NO: 6].

According to another embodiment the inventive trafficking sequence may comprise or consist of variants of the trafficking sequences as defined above. A "variant of a trafficking sequence" is preferably a sequence derived from a trafficking sequence as defined above, wherein the variant comprises a modification, for example, addition, (internal) deletion (leading to fragments) and/or substitution of at least one amino acid present in the trafficking sequence as defined above. Such (a) modification(s) typically comprise(s) 1 to 20, preferably 1 to 10 and more preferably 1 to 5 substitutions, additions and/or deletions of amino acids. Furthermore, the variant preferably exhibits a sequence identity with the trafficking sequence as defined above, more preferably with any of SEQ ID NOs: 5 to 8, of at least about 30%, 50%, 70%, 80%, 90%, 95%, 98% or even 99%.

Preferably, such a modification of the trafficking sequence leads to a trafficking sequence with increased or decreased stability. Alternatively, variants of the trafficking sequence can be designed to modulate intracellular localization of the inventive chimeric peptide. When added exogenously, such variants as defined above are typically designed such that the ability of the trafficking sequence to enter cells is retained (i.e. the uptake of the variant of the trafficking sequence into the cell is substantially similar to that of the native protein used a trafficking sequence). For example, alteration of the basic region thought to be important for nuclear localization (see e.g. Dang and Lee, J. Biol. Chem. 264: 18019-18023 (1989); Hauber et al., J. Virol. 63: 1181-1187 (1989); et al., J. Virol. 63: 1-8 (1989)) can result in a cytoplasmic location or partially cytoplasmic location of the trafficking sequence, and therefore, of the JNK inhibitor sequence as component of the inventive chimeric peptide. Additional to the above, further modifications may be introduced into the variant, e.g. by linking e.g. cholesterol or other lipid moieties to the trafficking sequence to produce a trafficking sequence having increased membrane solubility. Any of the above disclosed variants of the inventive trafficking sequences can be produced using techniques typically known to a skilled person (see e.g. Sambrook, J., Fritsch, E. F., Maniatis, T. (1989) Molecular cloning: A laboratory manual. 2nd edition. Cold Spring Harbor Laboratory, Cold Spring Harbor, N.Y.)

As a second domain the inventive chimeric peptide typically comprises an inventive JNK inhibitor sequence, selected from any of the inventive JNK inhibitor sequences as defined above, including variants, fragments and/or derivatives of these inventive JNK inhibitor sequences.

Both domains, i.e. the first and the second domain,(s) of the inventive chimeric peptide, may be linked such as to form a functional unit. Any method for linking the first and second domain(s) as generally known in the art may be applied.

According to one embodiment, the first and the second domain(s) of the inventive chimeric peptide are preferably linked by a covalent bond. A covalent bond, as defined herein, may be e.g. a peptide bond, which may be obtained by expressing the inventive chimeric protein as a fusion protein. Fusion proteins, as described herein, can be formed and used in ways analogous to or readily adaptable from standard recombinant DNA techniques, as described below. However, both domains may also be linked via side chains or may be linked by a chemical linker moiety.

The first and/or second domains of the inventive chimeric peptide may occur in one or more copies in the inventive chimeric peptide. If both domains are present in a single copy, the first domain may be linked either to the N-terminal or the C-terminal end of the second domain. If present in multiple copies, the first and second domain(s) may be arranged in any possible order. E.g. the first domain can be present in the inventive chimeric peptide in a multiple copy number, e.g. in two, three or more copies, which are preferably arranged in consecutive order. Then, the second domain may be present in a single copy occurring at the N- or C-terminus of the sequence comprising the first domain. Alternatively, the second domain may be present in a multiple copy number, e.g. in two, three or more copies, and the first domain may be present in a single copy. According to both alternatives, first and second domain(s) can take any place in a consecutive arrangement. Exemplary arrangements are shown in the following: e.g. first domain-first domain-first domain-second domain; first domain-first domain-second domain-first domain; first domain-second domain-first domain-first domain; or e.g. second domain-first domain-first domain-first domain. It is well understood for a skilled person that these examples are for illustration purposes only and shall not limit the scope of the invention thereto. Thus, the number of copies and the arrangement may be varied as defined initially.

Preferably, the first and second domain(s) may be directly linked with each other without any linker. Alternatively, they may be linked with each other via a linker sequence comprising 1 to 10, preferably 1 to 5 amino acids. Amino acids forming the linker sequence are preferably selected from glycine or proline as amino acid residues. More preferably, the first and second domain(s) may be separated by each other by a hinge of two, three or more proline residues between the first and second domain(s).

The inventive chimeric peptide as defined above, comprising at least one first and at least one second domain, may be composed of L-amino acids, D-amino acids, or a combination of both. Therein, each domain (as well as the linkers used) may be composed of L-amino acids, D-amino acids, or a combination of both (e.g. D-TAT and L-IB1(s) or L-TAT and D-IB1(s), etc.). Preferably, the inventive chimeric peptide comprises at least 1, preferably at least 3, more preferably at least 6 and even more preferably at least 10 L-amino acids and/or D-amino acids, wherein the D- and/or L-amino acids may be arranged in the inventive chimeric peptide in a block-wise, a non-blockwise or in an alternate manner.

According to a specific embodiment the inventive chimeric peptide comprises or consists of the L-amino acid chimeric peptides according to the generic L-TAT-IB peptide [NH$_2$—X$_n^b$-RKKRRQRRR-X$_n^b$—X$_n^a$-RPTTLXLXXXXXXQD-X$_n^b$-COOH, SEQ ID NO: 10], wherein X, X$_n^a$ and X$_n^b$ are preferably as defined above. More preferably, the inventive chimeric peptide comprises or consists of the L-amino acid chimeric peptide L-TAT-IB1 [NH$_2$-GRKKRRQRRRPPRPKRPTTLN-LFPQVPRSQD-COOH, SEQ ID NO: 9].

According to an alternative specific embodiment the inventive chimeric peptide comprises or consists of D-amino acid chimeric peptides of the above disclosed L-amino acid chimeric peptides. Exemplary D retro-inverso chimeric peptides according to the present invention are e.g. the generic D-TAT-IB peptide [NH$_2$—X$_n^b$-DQXXXXXXXLXLTTPRR-X$_n^a$—X$_n^b$-RRRQRRKKR-X$_n^b$-COOH, SEQ ID NO: 12]. Herein, X, X$_n^a$ and X$_n^b$ are preferably as defined above (preferably representing D amino acids). More preferably, the inventive chimeric peptide comprises or consists of D-amino acid chimeric peptides according to the TAT-IB1 peptide [NH$_2$-DQSRPVQPFLNLTTPRKPRPPRRRQRRKKRG-COOH, SEQ ID NO: 11].

The first and second domain(s) of the inventive chimeric peptide as defined above may be linked to each other by chemical or biochemical coupling carried out in any suitable manner known in the art, e.g. by establishing a peptide bond between the first and the second domain(s) e.g. by expressing the first and second domain(s) as a fusion protein, or e.g. by crosslinking the first and second domain(s) of the inventive chimeric peptide.

Many known chemical crosslinking methods are non-specific, i.e. they do not direct the point of coupling to any particular site on the transport polypeptide or cargo macromolecule. As a result, use of non-specific crosslinking agents may attack functional sites or sterically block active sites, rendering the conjugated proteins biologically inactive. Thus, preferably such crosslinking methods are used, which allow a more specific coupling of the first and second domain(s).

One way to increasing coupling specificity is a direct chemical coupling to a functional group present only once or a few times in one or both of the first and second domain(s) to be crosslinked. For example, cysteine, which is the only protein amino acid containing a thiol group, occurs in many proteins only a few times. Also, for example, if a polypeptide contains no lysine residues, a crosslinking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity.

Cysteine residues may be replaced when they occur in parts of a polypeptide sequence where their participation in a crosslinking reaction would otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for crosslinking purposes.

When a cysteine residue is introduced, introduction at or near the amino or carboxy terminus is preferred. Conventional methods are available for such amino acid sequence modifications, wherein the polypeptide of interest is produced by chemical synthesis or via expression of recombinant DNA.

Coupling of the first and second domain(s) can also be accomplished via a coupling or conjugating agent. There are several intermolecular crosslinking reagents which can be utilized (see for example, Means and Feeney, CHEMICAL MODIFICATION OF PROTEINS, Holden-Day, 1974, pp. 39-43). Among these reagents are, for example, N-succinimidyl 3-(2-pyridyldithio) propionate (SPDP) or N,N'-(1,3-phenylene) bismaleimide (both of which are highly specific for sulfhydryl groups and form irreversible linkages); N,N'-ethylene-bis-(iodoacetamide) or other such reagent having 6 to 11 carbon methylene bridges (which are relatively specific for sulfhydryl groups); and 1,5-difluoro-2,4-dinitrobenzene (which forms irreversible linkages with amino and tyrosine groups). Other crosslinking reagents useful for this purpose include: p,p'-difluoro-m, m'-dinitrodiphenylsulfone which forms irreversible crosslinkages with amino and phenolic groups); dimethyl adipimidate (which is specific for amino groups); phenol-1,4 disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Crosslinking reagents may be homobifunctional, i.e. having two functional groups that undergo the same reaction. A preferred homobifunctional crosslinking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible crosslinking of polypeptides that contain cysteine residues.

Crosslinking reagents may also be heterobifunctional. Heterobifunctional crosslinking agents have two different functional groups, for example an amine-reactive group and a thiol-reactive group, that will crosslink two proteins having free amines and thiols, respectively.

Examples of heterobifunctional crosslinking agents are succinimidyl 4-(N-maleimidomethyl)cyclohexane-1-carboxylate ("SMCC"), m-maleimidobenzoyl-N-hydroxysuccinimide ester ("MBS"), and succinimide 4-(p-maleimidophenyl)butyrate ("SMPB"), an extended chain analog of MBS. The succinimidyl group of these crosslinkers reacts with a primary amine, and the thiol-reactive maleimide forms a covalent bond with the thiol of a cysteine residue.

Crosslinking reagents often have low solubility in water. A hydrophilic moiety, such as a sulfonate group, may be added to the crosslinking reagent to improve its water solubility. In this respect, Sulfo-MBS and Sulfo-SMCC are examples of crosslinking reagents modified for water solubility, which may be used according to the present invention.

Many crosslinking reagents yield a conjugate that is essentially non-cleavable under cellular conditions. However, some crosslinking reagents contain a covalent bond, such as a disulfide, that is cleavable under cellular conditions. For example, Traut's reagent, dithiobis(succinimidylpropionate) ("DSP"), and N-succinimidyl 3-(2-pyridyldithio)propionate ("SPDP") are well-known cleavable crosslinkers. The use of a cleavable crosslinking reagent permits the cargo moiety to separate from the transport polypeptide after delivery into the target cell. Direct disulfide linkage may also be useful.

Numerous crosslinking reagents, including the ones discussed above, are commercially available. Detailed instructions for their use are readily available from the commercial suppliers. A general reference on protein crosslinking and conjugate preparation is: Wong, CHEMISTRY OF PROTEIN CONJUGATION AND CROSSLINKING, CRC Press (1991).

Chemical crosslinking may include the use of spacer arms. Spacer arms provide intramolecular flexibility or adjust intramolecular distances between conjugated moieties and thereby may help preserve biological activity. A spacer arm may be in the form of a polypeptide moiety that includes spacer amino acids, e.g. proline. Alternatively, a spacer arm may be part of the crosslinking reagent, such as in "long-chain SPDP" (Pierce Chem. Co., Rockford, Ill., cat. No. 21651 H).

Furthermore, variants, fragments or derivatives of one of the above disclosed chimeric peptides are disclosed herewith. With regard to fragments and variants it is generally referred to the definition given above for JNK inhibitor sequences.

Particularly, in the context of the present invention, a "variant of a chimeric peptide" is preferably a sequence derived from any of the sequences according to SEQ ID NOs: 9 to 12, wherein the chimeric variant comprises amino acid alterations of the inventive chimeric peptides according to SEQ ID NOs: 9 to 12. Such alterations typically comprise 1 to 20, preferably 1 to 10 and more preferably 1 to 5 substitutions, additions and/or deletions (leading to fragments) of amino acids according to SEQ ID NOs: 9 to 12, wherein the altered inventive chimeric peptide exhibits a sequence identity with any of the sequences according to SEQ ID NOs: 9, 10, 11 or 12 of at least about 30%, 50%, 70%, 80%, or 95%, 98%, or even 99%. Preferably, these variants retain the biological activity of the first and the second domain as contained in the inventive chimeric peptide, i.e. the trafficking activity of the first domain as disclosed above and the activity of the second domain for binding JNK and/or inhibiting the activation of at least one JNK activated transcription factor.

Accordingly, the inventive chimeric peptide also comprises fragments of the afore disclosed inventive chimeric peptides, particularly of the inventive chimeric peptide sequences according to SEQ ID NOs: 9, 10, 11 or 12. Thus, in the context of the present invention, a "fragment of the inventive chimeric peptide" is preferably a sequence derived any of the sequences according to SEQ ID NOs: 9, 10, 11 or 12, wherein the fragment comprises at least 4 contiguous amino acids of any of SEQ ID NOs: 9, 10, 11 or 12. This fragment preferably comprises a length which is sufficient to allow specific recognition of an epitope from any of these sequences and to transport the sequence into the cells, the nucleus or a further preferred location. Even more preferably, the fragment comprises 4 to 18, 4 to 15, or most preferably 4 to 10 contiguous amino acids of any of SEQ ID NOs: 9, 10, 11 or 12. Fragments of the inventive chimeric peptide further may be defined as a sequence sharing a sequence identity with any of the sequences according to SEQ ID NOs: 9, 10, 11 or 12 of at least about 30%, 50%, 70%, 80%, or 95%, 98%, or even 99%.

Finally, the inventive chimeric peptide also comprises derivatives of the afore disclosed inventive chimeric peptides, particularly of the inventive chimeric peptide sequences according to SEQ ID NOs: 9, 10, 11 or 12.

The present invention additionally refers to nucleic acid sequences encoding inventive JNK inhibitor sequences, inventive chimeric peptides, or their fragments, variants or derivatives as defined above. A preferable suitable nucleic acid encoding an inventive JNK inhibitor sequence is chosen from human IB1 nucleic acid (GenBank Accession No. (AF074091), rat IB1 nucleic acid (GenBank Accession No. AF 108959), or human IB2 (GenBank Accession No AF218778).

Nucleic acids encoding the inventive JNK inhibitor sequences or chimeric peptides may be obtained by any method known in the art (e.g. by PCR amplification using synthetic primers hybridizable to the 3'- and 5'-termini of the sequence and/or by cloning from a cDNA or genomic library using an oligonucleotide sequence specific for the given gene sequence).

Additionally, nucleic acid sequences are disclosed herein as well, which hybridize under stringent conditions with the appropriate strand coding for a (native) inventive JNK inhibitor sequence or chimeric peptide as defined above. Preferably, such nucleic acid sequences comprise at least 6 (contiguous) nucleic acids, which have a length sufficient to allow for specific hybridization. More preferably, such nucleic acid sequences comprise 6 to 38, even more preferably 6 to 30, and most preferably 6 to 20 or 6 to 10 (contiguous) nucleic acids.

"Stringent conditions" are sequence dependent and will be different in different circumstances. Generally, stringent conditions can be selected to be about 5° C. lower than the thermal melting point (TM) for the specific sequence at a defined ionic strength and pH. The TM is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may affect the stringency of hybridization (including, among others, base composition and size of the complementary strands), the presence of organic solvents and the extent of base mismatching, the combination of parameters is more important than the absolute measure of any one.

"High stringency conditions" may comprise the following, e.g. Step 1: Filters containing DNA are pretreated for 8 hours to overnight at 65° C. in buffer composed of 6*SSC, 50 mM Tris-HCl (pH 7.5), 1 mM EDTA, 0.02% PVP, 0.02% Ficoll, 0.02% BSA, and 500 µg/ml denatured salmon sperm DNA. Step 2: Filters are hybridized for 48 hours at 65° C. in the above prehybridization mixture to which is added 100 mg/ml denatured salmon sperm DNA and 5-20*10$^6$ cpm of $^{32}$P-labeled probe. Step 3: Filters are washed for 1 hour at 37° C. in a solution containing 2*SSC, 0.01% PVP, 0.01% Ficoll, and 0.01% BSA. This is followed by a wash in 0.1*SSC at 50° C. for 45 minutes. Step 4: Filters are autoradiographed. Other conditions of high stringency that may be used are well known in the art (see e.g. Ausubel et al., (eds.), 1993, Current Protocols in Molecular Biology, John Wiley and Sons, NY; and Kriegler, 1990, Gene Transfer and Expression, a Laboratory Manual, Stockton Press, NY).

"Moderate stringency conditions" can include the following: Step 1: Filters containing DNA are pretreated for 6 hours at 55° C. in a solution containing 6*SSC, 5*Denhardt's solution, 0.5% SDS and 100 mg/ml denatured salmon sperm DNA. Step 2: Filters are hybridized for 18-20 hours at 55° C. in the same solution with 5-20*10$^6$ cpm $^{32}$P-labeled probe added. Step 3: Filters are washed at 37° C. for 1 hour in a solution containing 2*SSC, 0.1% SDS, then washed twice for 30 minutes at 60° C. in a solution containing 1*SSC and 0.1% SDS. Step 4: Filters are blotted dry and exposed for autoradiography. Other conditions of moderate stringency that may be used are well-known in the art (see e.g. Ausubel et al., (eds.), 1993, Current Protocols in Molecular Biology, John Wiley and Sons, NY; and Kriegler, 1990, Gene Transfer and Expression, a Laboratory Manual, Stockton Press, NY).

Finally, "low stringency conditions" can include: Step 1: Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Step 2: Filters are hybridized for 18-20 hours at 40° C. in the same solution with the addition of 0.02% PVP, 0.02% Ficoll, 0.2% BSA, 100 µg/ml salmon sperm DNA, 10% (wt/vol) dextran sulfate, and 5-20×106 cpm $^{32}$P-labeled probe. Step 3: Filters are washed for 1.5 hours at 55 C in a solution containing 2×SSC, 25 mM Tris-HCl (pH 7.4), 5 mM EDTA, and 0.1% SDS. The wash solution is replaced with fresh solution and incubated an additional 1.5 hours at 60° C. Step 4: Filters are blotted dry and exposed for autoradiography. If necessary, filters are washed for a third time at 65-68° C. and reexposed to film. Other conditions of low stringency that may be used are well known in the art (e.g. as employed for cross-species hybridizations). See e.g. Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

The nucleic acid sequences provided by the present invention can be used to express inventive peptides, i.e. an inventive JNK inhibitor sequence or an inventive chimeric peptide for analysis, characterization or therapeutic use; as markers for tissues in which the corresponding (inventive) peptides are preferentially expressed (either constitutively or at a particular stage of tissue differentiation or development or in disease states). Other uses for the nucleic acids include, e.g. molecular weight markers in gel electrophoresis-based analysis of nucleic acids.

According to a further embodiment of the present invention, expression vectors are also provided for recombinant expression of one or more inventive JNK inhibitor sequences and/or chimeric peptides as defined above. The term "expression vector" is used herein to designate either circular or linear DNA or RNA, which is either double-stranded or single-stranded. It further comprises at least one inventive nucleic acid to be transferred into a host cell or into a unicellular or multicellular host organism. The inventive expression vector preferably comprises an inventive nucleic acid encoding the inventive JNK inhibitor sequence or a fragment or a variant thereof, or the inventive chimeric peptide, or a fragment or a variant thereof. Additionally, an expression vector according to the present invention preferably comprises appropriate elements for supporting expression including various regulatory elements, such as enhancers/promoters from viral, bacterial, plant, mammalian, and other eukaryotic sources that drive expression of the inserted polynucleotide in host cells, such as insulators, boundary elements, LCRs (e.g. described by Blackwood and Kadonaga (1998), Science 281, 61-63) or matrix/scaffold attachment regions (e.g. described by Li, Harju and Peterson, (1999), Trends Genet. 15, 403-408). In some embodiments, the regulatory elements are heterologous (i.e. not the native gene promoter). Alternately, the necessary transcriptional and translational signals may also be supplied by the native promoter for the genes and/or their flanking regions.

The term "promoter" as used herein refers to a region of DNA that functions to control the transcription of one or more inventive nucleic acid sequences, and that is structurally identified by the presence of a binding site for DNA-dependent RNA-polymerase and of other DNA sequences, which interact to regulate promoter function. A functional expression promoting fragment of a promoter is a shortened or truncated promoter sequence retaining the activity as a promoter. Promoter activity may be measured by any assay known in the art (see e.g. Wood, de Wet, Dewji, and DeLuca, (1984), Biochem Biophys. Res. Commun. 124, 592-596; Seliger and McElroy, (1960), Arch. Biochem. Biophys. 88, 136-141) or commercially available from Promega®).

An "enhancer region" as used in the inventive expression vector, typically refers to a region of DNA that functions to increase the transcription of one or more genes. More specifically, the term "enhancer", as used herein, is a DNA regulatory element that enhances, augments, improves, or ameliorates expression of a gene irrespective of its location and orientation vis-à-vis the gene to be expressed, and may be enhancing, augmenting, improving, or ameliorating expression of more than one promoter.

Promoter/enhancer sequences as defined above for the inventive expression vector, may utilize plant, animal, insect, or fungus regulatory sequences. For example, promoter/enhancer elements can be used from yeast and other fungi (e.g. the GAL4 promoter, the alcohol dehydrogenase promoter, the phosphoglycerol kinase promoter, the alkaline phosphatase promoter). Alternatively, or in addition, they may include animal transcriptional control regions, e.g. (i) the insulin gene control region active within pancreatic β-cells (see e.g. Hanahan, et al., 1985. Nature 315: 115-122); (ii) the immunoglobulin gene control region active within lymphoid cells (see e.g. Grosschedl, et al., 1984, Cell 38: 647-658); (iii) the albumin gene control region active within liver (see e.g. Pinckert, et al., 1987. Genes and Dev 1: 268-276; (iv) the myelin basic protein gene control region active within brain oligodendrocyte cells (see e.g. Readhead, et al., 1987, Cell 48: 703-712); and (v) the gonadotropin-releasing hormone gene control region active within the hypothalamus (see e.g. Mason, et al., 1986, Science 234: 1372-1378), and the like.

Additionally, the inventive expression vector may comprise an amplification marker. This amplification marker may be selected from the group consisting of, e.g. adenosine deaminase (ADA), dihydrofolate reductase (DHFR), multiple drug resistance gene (MDR), ornithine decarboxylase (ODC) and N-(phosphonacetyl)-L-aspartate resistance (CAD). Amplification of the gene encoding the above defined proteins, i.e. the protein of interest (POI) and/or the inventive fusion protein, allows to increase the expression level of these proteins upon integration of the vector in a cell (Kaufman et al. (1985), Mol. Cell Biol. 5, 1750-1759).

Exemplary expression vectors or their derivatives suitable for the present invention particularly include, e.g. human or animal viruses (e.g. vaccinia virus or adenovirus); insect viruses (e.g. baculovirus); yeast vectors; bacteriophage vectors (e.g. lambda phage); plasmid vectors and cosmid vectors.

The present invention additionally provides a variety of host-vector systems, which may be utilized to express the peptide coding sequence(s) of inventive nucleic acids as defined above. These include, but are not limited to: (i) mammalian cell systems that are infected with vaccinia virus, adenovirus, and the like; (ii) insect cell systems infected with baculovirus and the like; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

Preferably, a host cell strain, suitable for such a host-vector system, may be selected that modulates the expression of inserted sequences of interest, or modifies or processes expressed peptides encoded by the sequences in the specific manner desired. In addition, expression from certain promoters may be enhanced in the presence of certain inducers in a selected host strain; thus facilitating control of the expression of a genetically-engineered peptide. Moreover, different host cells possess characteristic and specific mechanisms for the translational and post-translational processing and modification (e.g. glycosylation, phosphorylation, and the like) of expressed peptides. Appropriate cell lines or host systems may thus be chosen to ensure the desired modification and processing of the foreign peptide is achieved. For example, peptide expression within a bacterial system can be used to produce an non-glycosylated core peptide; whereas expression within mammalian cells ensures "native" glycosylation of a heterologous peptide.

The present invention further provides antibodies directed against the inventive JNK inhibitor sequences and/or inventive chimeric peptides. Furthermore, efficient means for production of antibodies specific for JNK inhibitor sequences according to the present invention, or for inventive chimeric peptides containing such an inhibitor sequence, are provided.

According to the invention, JNK inhibitor sequences and/or inventive chimeric peptides, as well as, fragments, variants or derivatives thereof, may be utilized as immunogens to generate antibodies that immunospecifically bind these peptide components. Such antibodies include, e.g. polyclonal, monoclonal, chimeric, single chain, Fab fragments and a Fab expression library. In a specific embodiment the present invention provides antibodies to inventive chimeric peptides or to JNK inhibitor sequences as defined above. Various procedures known within the art may be used for the production of these inventive antibodies.

By way of example, various host animals may be immunized for production of polyclonal antibodies by injection with any inventive chimeric peptide or JNK inhibitor sequence as defined above. Various adjuvants may be used thereby to increase the immunological response which include, but are not limited to, Freund's (complete and incomplete) adjuvant, mineral gels (e.g. aluminum hydroxide), surface active substances (e.g. lysolecithin, pluronic polyols, polyanions, peptides, oil emulsions, dinitrophenol, etc.), CpG, polymers, Pluronics, and human adjuvants such as Bacille Calmette-Guerin and Corynebacterium parvum.

For preparation of monoclonal antibodies directed towards an inventive chimeric peptide or JNK inhibitor sequence as defined above, any technique may be utilized that provides for the production of antibody molecules by continuous cell line culture. Such techniques include, but are not limited to, the hybridoma technique (see Kohler and Milstein, 1975. Nature 256: 495-497); the trioma technique; the human B-cell hybridoma technique (see Kozbor, et al., 1983, Immunol Today 4: 72) and the EBV hybridoma technique to produce human monoclonal antibodies (see Cole, et al., 1985. In: Monoclonal Antibodies and Cancer Therapy, Alan R. Liss, Inc., pp. 77-96). Human monoclonal antibodies may be utilized in the practice of the present invention and may be produced by the use of human hybridomas (see Cote, et al., 1983. Proc Natl Acad Sci USA 80: 2026-2030) or by transforming human B-cells with Epstein Barr Virus in vitro (see Cole, et al., 1985. In: Monoclonal Antibodies and Cancer Therapy (Alan R. Liss, Inc., pp. 77-96).

According to the invention, techniques can be adapted for the production of single-chain antibodies specific to the inventive JNK inhibitor sequences and/or inventive chimeric peptides (see e.g. U.S. Pat. No. 4,946,778). In addition, methods can be adapted for the construction of Fab expression libraries (see e.g. Huse et al., 1989. Science 246: 1275-1281) to allow rapid and effective identification of monoclonal Fab fragments with the desired specificity for these inventive JNK inhibitor sequences and/or inventive chimeric peptides as defined above. Non-human antibodies can be "humanized" by techniques well known in the art (see e.g. U.S. Pat. No. 5,225,539). Antibody fragments that contain the idiotypes to a JNK inhibitor sequences and/or inventive chimeric peptide may be produced by techniques known in the art including, e.g. (i) a F(ab')$_2$ fragment produced by pepsin digestion of an antibody molecule; (ii) a Fab fragment generated by reducing the disulfide bridges of an F(ab')$_2$ fragment; (iii) a Fab fragment generated by the treatment of the antibody molecule with papain and a reducing agent and (iv) Fv fragments.

In one embodiment of this invention, methods for the screening of inventive antibodies that possess the desired specificity include, but are not limited to, enzyme-linked immunosorbent assay (ELISA) and other immunologically-mediated techniques known within the art. In a specific embodiment, selection of antibodies that are specific to a particular epitope of an inventive JNK inhibitor sequence and/or an inventive chimeric peptide (e.g. a fragment thereof typically comprising a length of from 5 to 20, preferably 8 to 18 and most preferably 8 to 11 amino acids) is facilitated by generation of hybridomas that bind to the fragment of an inventive JNK inhibitor sequence and/or an inventive chimeric peptide possessing such an epitope. These antibodies that are specific for an epitope as defined above are also provided herein.

The inventive antibodies may be used in methods known within the art referring to the localization and/or quantification of an inventive JNK inhibitor sequence (and/or correspondingly to an inventive chimeric peptide), e.g. for use in measuring levels of the peptide within appropriate physiological samples, for use in diagnostic methods, or for use in imaging the peptide, and the like.

The inventive JNK inhibitor sequences, chimeric peptides, and/or nucleic acids of the invention can be formulated in pharmaceutical compositions, also encompassed herewith. These compositions may comprise, in addition to one of these substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal or patch routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is preferably in a "prophylactically effective amount or a "therapeutically effective amount" (as the case may be), this being sufficient to show benefit to the individual. The actual amount administered, and rate and time-course of administration, will depend on the nature and severity of what is being treated.

Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in REMINGTON'S PHARMACEUTICAL SCIENCES, 16th edition, Osol, A. (ed), 1980.

Alternatively, targeting therapies may be used to deliver the inventive JNK inhibitor sequences, chimeric peptides, and nucleic acids of the invention more specifically to certain types of cell, by the use of targeting systems such as (a targeting) antibody or cell specific ligands. Antibodies used for targeting are typically specific for cell surface proteins of cells associated with any of the diseases as defined below. By way of example, these antibodies may be directed to cell surface antibodies such as e.g. B cell-associated surface proteins such as MHC class II DR protein, CD18 (LFA-1 beta chain), CD45RO, CD40 or Bgp95, or cell surface proteins selected from e.g. CD2, CD2, CD4, CD5, CD7, CD8, CD9, CD10, CD13, CD16, CD19, CD20, CD21, CD22, CD23, CD24, CD25, CD30, CD33, CD34, CD38, CD39, CD4, CD43, CD45, CD52, CD56, CD68, CD71, CD138, etc. Targeting constructs may be typically prepared by covalently binding the inventive JNK inhibitor sequences, chimeric peptides, and nucleic acids to an antibody specific for a cell surface protein or by binding to a cell specific ligand. Proteins may e.g. be bound to such an antibody or may be attached thereto by a peptide bond or by chemical coupling, crosslinking, etc. The targeting therapy may then be carried out by administering the targeting construct in a pharmaceutically efficient amount to a patient by any of the administration routes as defined below, e.g. intraperitoneal, nasal, intravenous, oral and patch delivery routes. Preferably, the inventive JNK inhibitor sequences, chimeric peptides, or nucleic acids of the invention attached to the targeting antibodies or cell specific ligands as defined above, may be released in vitro or in vivo, e.g. by hydrolysis of the covalent bond, by peptidases or by any other suitable method. Alternatively, if the inventive JNK inhibitor sequences, chimeric peptides, or nucleic acids of the invention are attached to a small cell specific ligand, release of the ligand may not be carried out. If present at the cell surface, the inventive chimeric peptides may enter the cell upon the activity of its trafficking sequence. Targeting may be desirable for a variety of reasons; for example if the inventive JNK inhibitor sequences, chimeric peptides, and nucleic acids of the invention are unacceptably toxic or if it would otherwise require a too high dosage.

Instead of administering the inventive JNK inhibitor sequences and/or chimeric peptides of the invention directly, they could be produced in the target cells by expression from an encoding gene introduced into the cells, e.g. from a viral vector to be administered. The viral vector typically encodes the inventive JNK inhibitor sequences and/or chimeric peptides of the invention. The vector could be targeted to the specific cells to be treated. Moreover, the vector could contain regulatory elements, which are switched on more or less selectively by the target cells upon defined regulation. This technique represents a variant of the VDEPT technique (virus-directed enzyme prodrug therapy), which utilizes mature proteins instead of their precursor forms.

Alternatively, the inventive JNK inhibitor sequences and/or chimeric peptides could be administered in a precursor form by use of an antibody or a virus. The inventive JNK inhibitor sequences and/or chimeric peptides may then be converted into the active form by an activating agent produced in, or targeted to, the cells to be treated. This type of approach is sometimes known as ADEPT (antibody-directed enzyme prodrug therapy) or VDEPT (virus-directed enzyme prodrug therapy); the former involving targeting the activating agent to the cells by conjugation to a cell-specific antibody, while the latter involves producing the activating agent, e.g. a JNK inhibitor sequence or the chimeric peptide, in a vector by expression from encoding DNA in a viral vector (see for example, EP-A-415731 and WO 90/07936).

The present invention further encompasses the use of inventive JNK inhibitor sequences, inventive chimeric peptides and/or inventive nucleic acid sequences, for preparing a pharmaceutical composition, e.g. as defined above, for preventing and/or treating cell-proliferative disorders associated with JNK activation in a subject ("JNK associated disorder"). Typically, such a pharmaceutical composition used according to the present invention includes as an active component, e.g.: (i) any one or more of the inventive JNK inhibitor sequences and/or inventive chimeric peptides, and/or variants, fragments or derivatives thereof; and/or (ii) nucleic acids encoding an inventive JNK inhibitor sequence and/or an inventive chimeric peptide and/or variants or fragments thereof, and/or (iii) cells comprising any one or more of the inventive JNK inhibitor sequences and/or inventive chimeric peptides, and/or variants, fragments or derivatives thereof and/or (iv) cells transfected with a vector and/or nucleic acids encoding an inventive JNK inhibitor sequence and/or an inventive chimeric peptide and/or variants or fragments thereof.

Prevention and/or treatment according to the present invention typically includes administration of an inventive pharmaceutical composition as defined above. The term "modulate" includes the suppression of expression of JNK when it is over-expressed. It also includes suppression of phosphorylation of c-jun, ATF2 or NFAT4, for example, by using a peptide of any one or more of SEQ ID NOs: 1-4 and/or 9-12 as a competitive inhibitor of the natural c-jun, ATF2 and NFAT4 binding site in a cell. The term "modulate" also includes suppression of hetero- and homomeric complexes of transcription factors made up of c-jun, ATF2, or NFAT4 and their related partners, such as for example the AP-1 complex that is made up of c-jun, AFT2 and c-fos. When a cell proliferative disorder is associated with JNK overexpression, such suppressive JNK inhibitor sequences can be introduced to a cell. In some instances, "modulate" may include the increase of JNK expression, for example by use of an IB peptide-specific antibody that blocks the binding of an IB-peptide to JNK, thus preventing JNK inhibition by the IB-related peptide.

Prevention and/or treatment of a subject with the inventive pharmaceutical composition as disclosed above may be typically accomplished by administering (in vivo) an ("therapeutically effective") amount of said pharmaceutical composition to a subject, wherein the subject may be e.g. any mammal, e.g. a human, a primate, mouse, rat, dog, cat, cow, horse or pig. The term "therapeutically effective" means that the active component of the pharmaceutical composition is of sufficient quantity to ameliorate the JNK associated disorder.

The term "cell-proliferative disorder" or "JNK associated disorder" as used above typically denotes malignant as well as non-malignant cell populations in vivo and in vitro that often appear to differ morphologically and functionally from the surrounding tissue and which are typically characterized by aberrant levels of JNK. An "aberrant level of JNK" is intended to mean an increased or decreased level of JNK in a part of the subject to be treated relative to that present in an analogous unaffected part of a subject not having the disorder.

For example, the inventive pharmaceutical compositions may be useful in preventing, and/or treating malignancies of the various organ systems, in which activation of JNK has often been demonstrated, e.g. lung, breast, lymphoid, gastrointestinal, and genito-urinary tract as well as adenocarcinomas which include malignancies such as most colon cancers, renal-cell carcinoma, prostate cancer, non-small cell carcinoma of the lung, cancer of the small intestine and cancer of the esophagus. Leukemia, disorders or pathophysiologies associated with oncogenic transformation as well as cancers with Bcr-Abl oncogenic transformations that clearly require activation of JNK are also included.

The inventive pharmaceutical compositions are also applicable in preventing and/or treating non-malignant or immunological-related cell proliferative diseases such as psoriasis, pemphigus vulgaris, Behcet's syndrome, acute respiratory distress syndrome (ARDS), ischemic heart disease, post-dialysis syndrome, rheumatoid arthritis, acquired immune deficiency syndrome, vasculitis, septic shock and other types of acute inflammation, and lipid histiocytosis. Especially preferred are immunopathological disorders. Essentially, any disorder, which is etiologically linked to JNK kinase activity, is considered susceptible to prevention or treatment, e.g. disorders or pathophysiologies associated with activation of JNK in a cell or cells as defined above, e.g. restenosis, hearing loss, ear trauma, ischemia, stroke and/or disorders or pathophysiologies associated with maturation and differentiation of immune cells, reperfusion injuries, hypoxia, apoptosis-related diseases (e.g. occurring in viral infections (e.g. AIDS), autoimmune diseases, neurodegenerative disorders (e.g. stroke, brain trauma, spinal cord injury, amyotrophic lateral sclerosis (ALS), Huntington's disease, Alzheimer's disease, and Parkinson's disease), cardiovascular disease, osteoporosis and aging), response to stressful stimuli, and with secondary effects due to treatment with e.g. proinflammatory cytokines. The inventive pharmaceutical composition may also be used to treat or prevent effects associated with diabetes or with cellular shear stress, such as in pathological states induced by arterial hypertension, including heart and cardiac hypertrophy and arteriosclerotic lesions, and at bifurcations of blood vessels, and the like, by ionizing radiation, as used in radiotherapy and ultraviolet light (UV lights), by free radicals, DNA damaging agents, including chemotherapeutic drugs, by ischemia/reperfusion injuries, by hypoxia; and/or hypo- and hyperthermia. Finally, in the context of the above mentioned diseases, disorders or pathophysiologies, the inventive pharmaceutical composition may be used to inhibit expression of genes whose expression increases in the presence of an active JNK polypeptide. These genes and gene products typically include e.g. proinflammatory cytokines. Such cytokines are found in all forms of inflammatory, auto-inflammatory, immune and autoimmune diseases, degenerative diseases, myopathies, cardiomyopathies, and graft rejection.

The inventive JNK inhibitor sequences, inventive chimeric peptides or inventive nucleic acid sequences further may be used in any situation in which inhibition of JNK activity is desired, since JNKs and all its isoforms participate in the development and establishment of pathological states or in pathways thereof Such use can include in vitro applications, ex vivo, and in vivo applications.

Accordingly, inventive nucleic acids as defined above may be utilized in a specific embodiment of the present invention to modulate activated JNK signaling pathways by way of gene therapy, preferably for treating one of the conditions, diseases, and/or disorders as defined above. In this context, gene therapy refers to therapy that is performed by administration of a specific inventive nucleic acid to a subject, e.g. by way of a pharmaceutical composition as defined above, wherein the inventive nucleic acid(s) exclusively comprise(s) L-amino acids. In this embodiment of the present invention, the nucleic acid produces its encoded peptide(s), which then serve(s) to exert a therapeutic effect by modulating function of the disease or disorder. Any of the methods relating to gene therapy available within the art may be used in the practice of the present invention (see e.g. Goldspiel, et al., 1993. Clin Pharm 12: 488-505).

In a preferred embodiment, the inventive nucleic acid used for gene therapy is part of an expression vector expressing any one or more of the inventive IB-related peptides, i.e. an inventive JNK inhibitor sequence and/or an inventive chimeric peptide, or fragments or derivatives thereof, within a suitable host. In a specific embodiment, such an expression vector possesses a promoter that is operably-linked to coding region(s) of a JNK inhibitor sequence. The promoter may be defined as above, e.g. inducible or constitutive, and, optionally, tissue-specific.

In another specific embodiment, a inventive nucleic acid molecule is used for gene therapy, in which the coding sequences of the inventive nucleic acid molecule (and any other desired sequences thereof) are flanked by regions that promote homologous recombination at a desired site within the genome, thus providing for intra-chromosomal expression of nucleic acids (see e.g. Koller and Smithies, 1989. Proc Natl Acad Sci USA 86: 8932-8935).

Delivery of the inventive nucleic acid for the into a patient purpose of gene therapy may be either direct (i.e. the patient is directly exposed to the nucleic acid or nucleic acid-containing vector) or indirect (i.e. cells are first transformed with the nucleic acid in vitro, then transplanted into the patient). These two approaches are known, respectively, as in vivo or ex vivo gene therapy. In a specific embodiment of the present invention, a nucleic acid is directly administered in vivo, where it is expressed to produce the encoded product. This may be accomplished by any of numerous methods known in the art including, e.g. constructing the nucleic acid as part of an appropriate nucleic acid expression vector and administering the same in a manner such that it becomes intracellular (e.g. by infection using a defective or attenuated retroviral or other viral vector; see U.S. Pat. No. 4,980,286); directly injecting naked DNA; using microparticle bombardment (e.g. a "GeneGun"; Biolistic, DuPont); coating the nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see e.g. Wu and Wu, 1987. J Biol Chem 262: 4429-4432), which can be used to "target" cell types that specifically express the receptors of interest, etc.

An additional approach to gene therapy in the practice of the present invention involves transferring a gene into cells in in vitro tissue culture by such methods as electroporation, lipofection, calcium phosphate-mediated transfection, viral infection, or the like. Generally, the method of transfer includes the concomitant transfer of a selectable marker to the cells. The cells are then placed under selection pressure (e.g. antibiotic resistance) so as to facilitate the isolation of those cells that have taken up, and are expressing, the transferred gene. Those cells are then delivered to a patient. In a specific embodiment, prior to the in vivo administration of the resulting recombinant cell, the nucleic acid is introduced into a cell by any method known within the art including e.g. transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methods that ensure that the necessary developmental and physiological functions of the recipient cells are not disrupted by the transfer. See e.g. Loeffler and Behr, 1993. Meth Enzymol 217: 599-618. The chosen technique should provide for the stable transfer of the nucleic acid to the cell, such that the nucleic acid is expressible by the cell. Preferably, the transferred nucleic acid is heritable and expressible by the cell progeny.

In preferred embodiments of the present invention, the resulting recombinant cells may be delivered to a patient by various methods known within the art including, e.g. injection of epithelial cells (e.g. subcutaneously), application of recombinant skin cells as a skin graft onto the patient, and intravenous injection of recombinant blood cells (e.g. hematopoietic stem or progenitor cells). The total amount of cells that are envisioned for use depend upon the desired effect, patient state, and the like, and may be determined by one skilled within the art. Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, Cell 71: 973-985), hematopoietic stem or progenitor cells, e.g. as obtained from bone marrow, umbilical cord blood, peripheral blood, fetal liver, and the like. In a preferred embodiment, the cells utilized for gene therapy are autologous to the patient.

According to a further embodiment, the inventive JNK inhibitor sequences, inventive chimeric peptides, inventive nucleic acid sequences or antibodies to inventive JNK inhibitor sequences or to inventive chimeric peptides may be utilized in (in vitro) assays (e.g. immunoassays) to detect, prognose, diagnose, or monitor various conditions, diseases, and/or disorders as defined above, or monitor the treatment thereof. The immunoassay may be performed by a method comprising contacting a sample derived from a patient with an antibody to an inventive JNK inhibitor sequence, an inventive chimeric peptide, or an inventive nucleic acid sequence, under conditions such that immunospecific-binding may occur, and subsequently detecting or measuring the amount of any immunospecific-binding by the antibody. In a specific embodiment, an antibody specific for an inventive JNK inhibitor sequence, inventive chimeric peptide or inventive nucleic acid sequence may be used to analyze a tissue or serum sample from a patient for the presence of JNK or a JNK inhibitor sequence; wherein an aberrant level of JNK is indicative of a diseased condition. The immunoassays that may be utilized include, but are not limited to, competitive and non-competitive assay systems using techniques such as Western Blots, radioimmunoassays (RIA), enzyme linked immunosorbent assay (ELISA), "sandwich" immunoassays, immunoprecipitation assays, precipitin reactions, gel diffusion precipitin reactions, immunodiffusion assays, agglutination assays, fluorescent immunoassays, complement-fixation assays, immunoradiometric assays, and protein-A immunoassays, etc. Alternatively, (in vitro) assays may be performed by delivering the inventive JNK inhibitor sequences, inventive chimeric peptides, inventive nucleic acid sequences or antibodies to inventive JNK inhibitor sequences or to inventive chimeric peptides to target cells typically selected from e.g. cultured animal cells, human cells or micro-organisms, and to monitor the cell response by biophysical methods typically known to a skilled person. The target cells typically used therein may be cultured cells (in vitro) or in vivo cells, i.e. cells composing the organs or tissues of living animals or humans, or microorganisms found in living animals or humans.

The present invention additionally provides kits for diagnostic or therapeutic use that include one or more containers containing inventive JNK inhibitor sequences, inventive chimeric peptides, inventive nucleic acid sequences and/or antibodies to inventive JNK inhibitor sequences or to inventive chimeric peptides, e.g. an anti-JNK inhibitor sequence antibody and, optionally, a labeled binding partner to the antibody. The label incorporated thereby into the antibody may include, but is not limited to, a chemiluminescent, enzymatic, fluorescent, colorimetric or radioactive moiety. In another specific embodiment, kits for diagnostic use are provided which comprise one or more containers containing nucleic acids that encode, or alternatively, that are the complement to, an inventive JNK inhibitor sequence and/or an inventive chimeric peptide, optionally, a labeled binding partner to these nucleic acids, are also provided. In an alternative specific embodiment, the kit may comprise, in one or more containers, a pair of oligonucleotide primers (e.g. each 6-30 nucleotides in length) that are capable of acting as amplification primers for polymerase chain reaction (PCR; see e.g. Innis, et al., 1990. PCR PROTOCOLS, Academic Press, Inc., San Diego, Calif.), ligase chain reaction, cyclic probe reaction, and the like, or other methods known within the art used in context with the inventive nucleic acids. The kit may, optionally, further comprise a predetermined amount of a purified inventive JNK inhibitor sequence, an inventive chimeric peptide, or nucleic acids encoding these, for use as a diagnostic, standard, or control in the assays.

The present invention is not to be limited in scope by the specific embodiments described herein. Indeed, various modifications of the invention in addition to those described herein will become apparent to those skilled in the art from the foregoing description and accompanying figures. Such modifications fall within the scope of the appended claims.

Various publications are cited herein, the disclosures of which are incorporated by reference in their entirety.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting. Other features and advantages of the invention will be apparent from the following detailed description and claims.

DESCRIPTION OF FIGURES

FIGS. 1A-C are diagrams showing alignments of conserved JBD domain regions in the indicated transcription factors. JNK inhibitor sequences were identified by inspecting these sequence alignments. The results of this alignment are exemplarily shown in FIGS. 1A-1C. FIG. 1A depicts the region of highest homology between the JBDs of IB1, IB2, c-Jun and ATF2. Panel B depicts the amino acid sequence of the JBDs of L-IB1(s) and L-IB1 for comparative reasons. Fully conserved residues are indicated by asterisks, while residues changed to Ala in the GFP-JBD$_{23Mut}$ vector are indicated by open circles. FIG. 1 C shows the amino acid sequences of chimeric proteins that include a JNK inhibitor sequence and a trafficking sequence. In the example shown, the trafficking sequence is derived from the human immunodeficiency virus (HIV) TAT polypeptide, and the JNK inhibitor sequence is derived from an IB1(s) polypeptide. Human, mouse, and rat sequences are identical in Panels B and C.

FIG. 2 is a diagram showing sequences of generic TAT-IB fusion peptides from human, mouse and rat.

FIG. 3 depicts the results from the evaluation of the neuroprotection against focal cerebral ischemia in a permanent MCAO model. Determination of the efficacy of the protection was carried out at different doses (see FIG. 3). As can be seen from FIG. 3, at least doses of 11 mg/kg, 3 mg/kg, 0.3 mg/kg and 0.03 mg/kg, contribute to a cerebral protection. The best protection is observed at the dose of 0.03 mg/kg.

Figure 4:
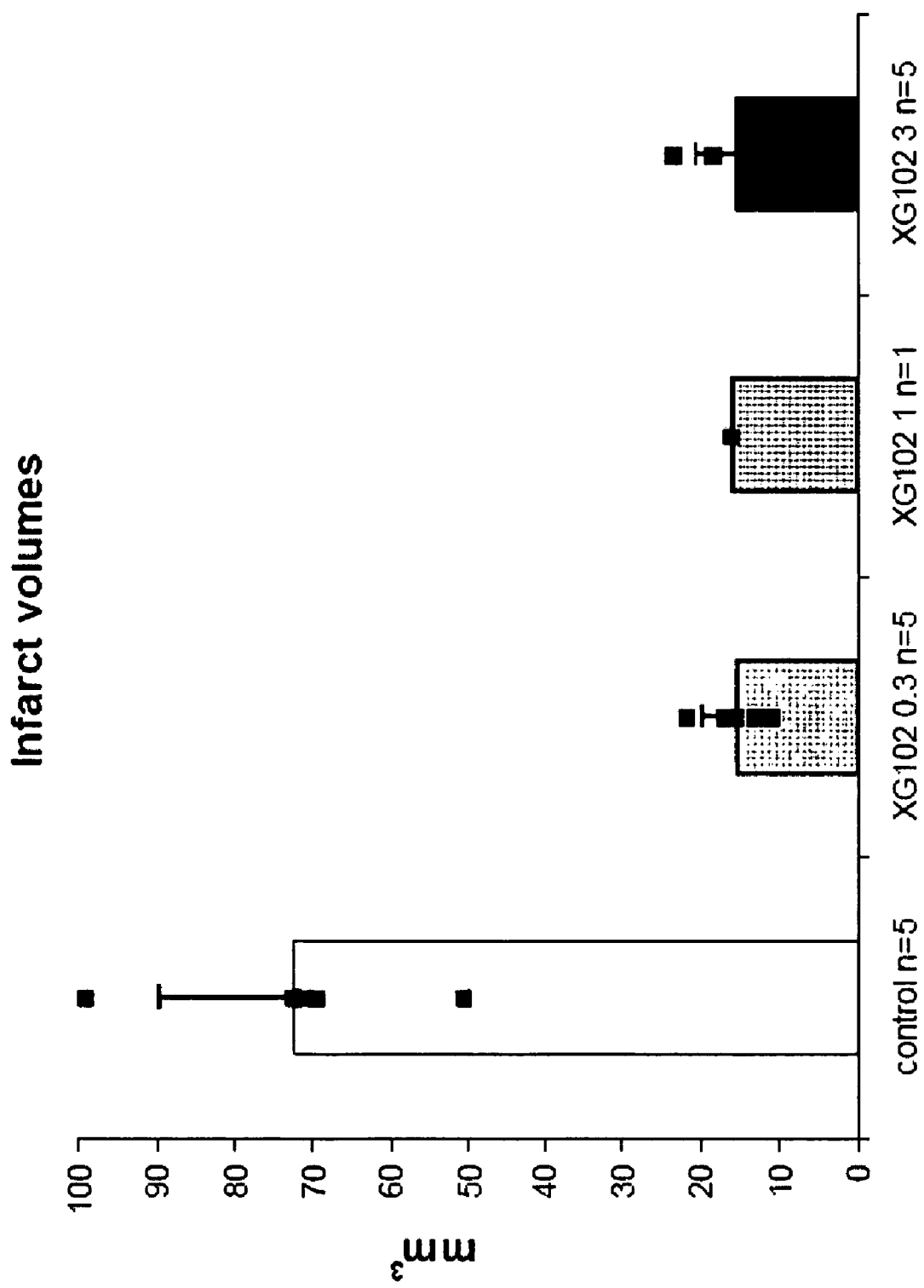
FIG. 4 illustrates the evaluation of neuroprotection by an inventive chimeric peptide according to SEQ ID NO: 11 after i.v. administration against focal cerebral ischemia, in a transient MCAO model. Subsequent to provoking ischemia in adult mice, the mice were killed 48 h after reperfusion. Serial cryostat sections were prepared and infarct volumes were calculated. As can be seen from FIG. 4, the inventive chimeric peptide provides efficient neuroprotection.

FIG. 4 illustrates the evaluation of neuroprotection by an inventive chimeric peptide according to SEQ ID NO: 11 after i.v. administration against focal cerebral ischemia, in a transient MCAO model. Subsequent to provoking ischemia in adult mice, the mice were killed 48 h after reperfusion. Serial cryostat sections were prepared and infarct volumes were calculated. As can be seen from FIG. 4, the inventive chimeric peptide provides efficient neuroprotection.

Figure 5:
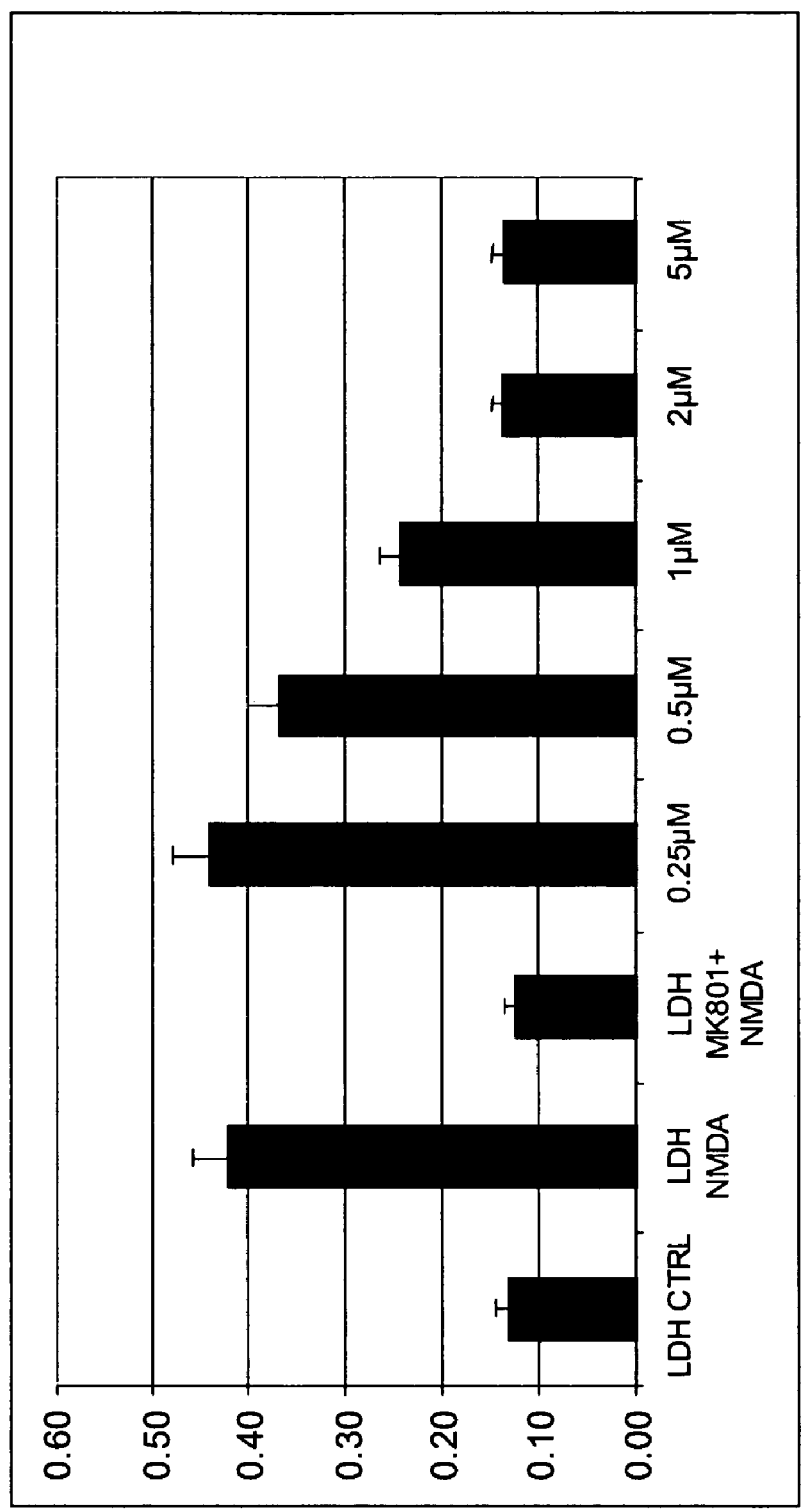
FIG. 5 shows the results of an assay on neuronal cultures carried out by measuring LDH release following NMDA stimulation. The results clearly indicate a neuroprotective effect of the inventive chimeric D-JNKI1 peptide (SEQ ID NO: 11), since degenerative changes due to NMDA exposure were completely inhibited as indicated by the absence of significant LDH release above controls.

FIG. 5 shows the results of an assay on neuronal cultures carried out by measuring LDH release following NMDA stimulation. The results clearly indicate a neuroprotective effect of the inventive chimeric D-JNKI 1 peptide (SEQ ID NO: 11), since degenerative changes due to NMDA exposure were completely inhibited as indicated by the absence of significant LDH release above controls.

Figure 6:
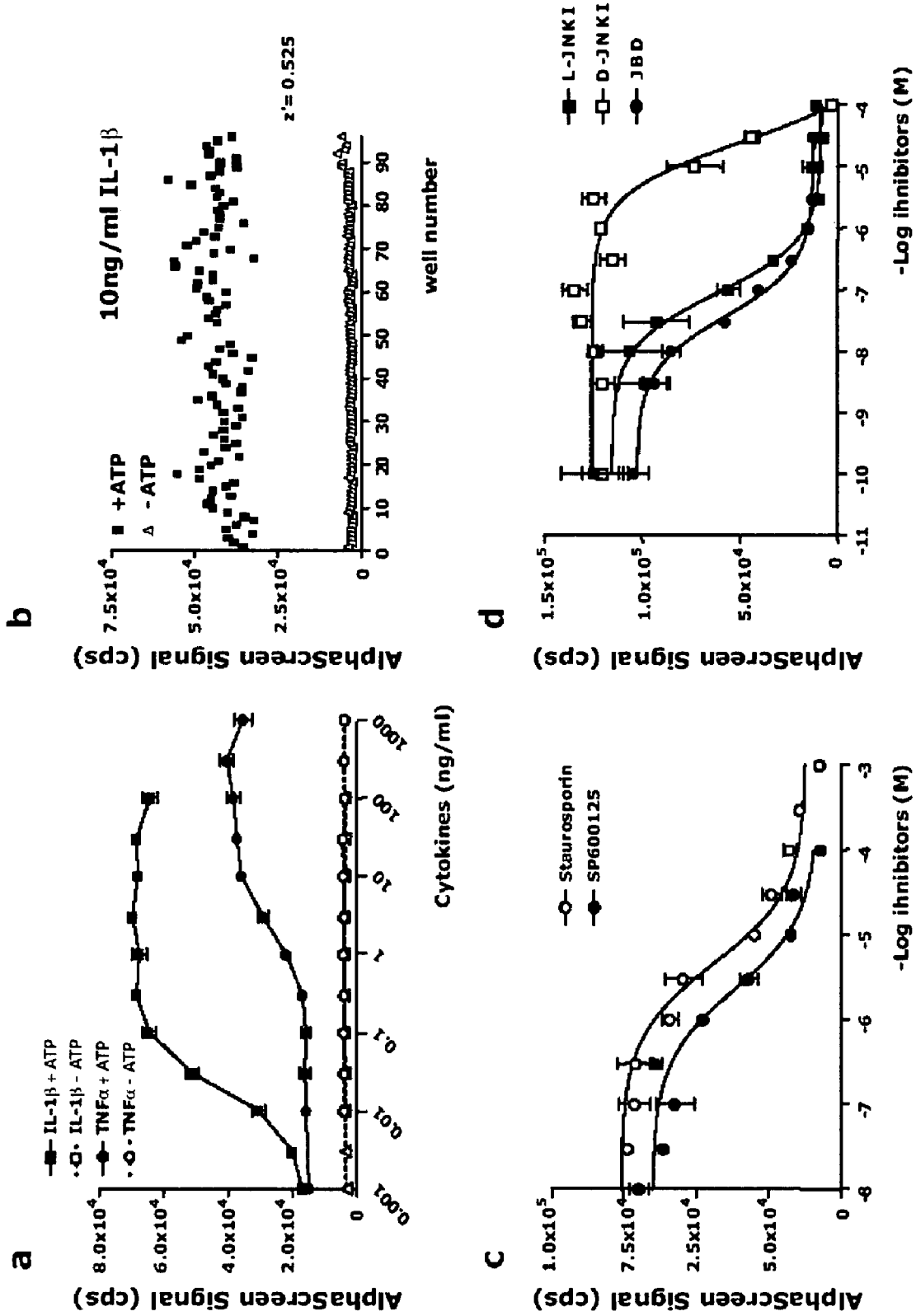
FIG. 6 depicts the results of the inhibition of endogeneous JNK-activity in HepG2 cells using inventive fusion peptides according to SEQ ID NOs: 9 and 11 in an one-well approach. As can be seen from FIG. 6, particularly panel d in FIG. 6, D-TAT-IB1(s) according to SEQ ID NO: 11 (here abbreviated as D-JNKI) effectively inhibits JNK activity, even better than L-TAT-IB1(s) according to SEQ ID NO: 9 (here abbreviated as L-JNKI).

FIG. 6 depicts the results of the inhibition of endogeneous JNK-activity in HepG2 cells using inventive fusion peptides according to SEQ ID NOs: 9 and 11 in an one-well approach. As can be seen from FIG. 6, particularly panel d in FIG. 6, D-TAT-IB1(s) according to SEQ ID NO: 11 (here abbreviated as D-JNKI) effectively inhibits JNK activity, even better than L-TAT-IB1(s) according to SEQ ID NO: 9 (here abbreviated as L-JNKI).

Figure 7:
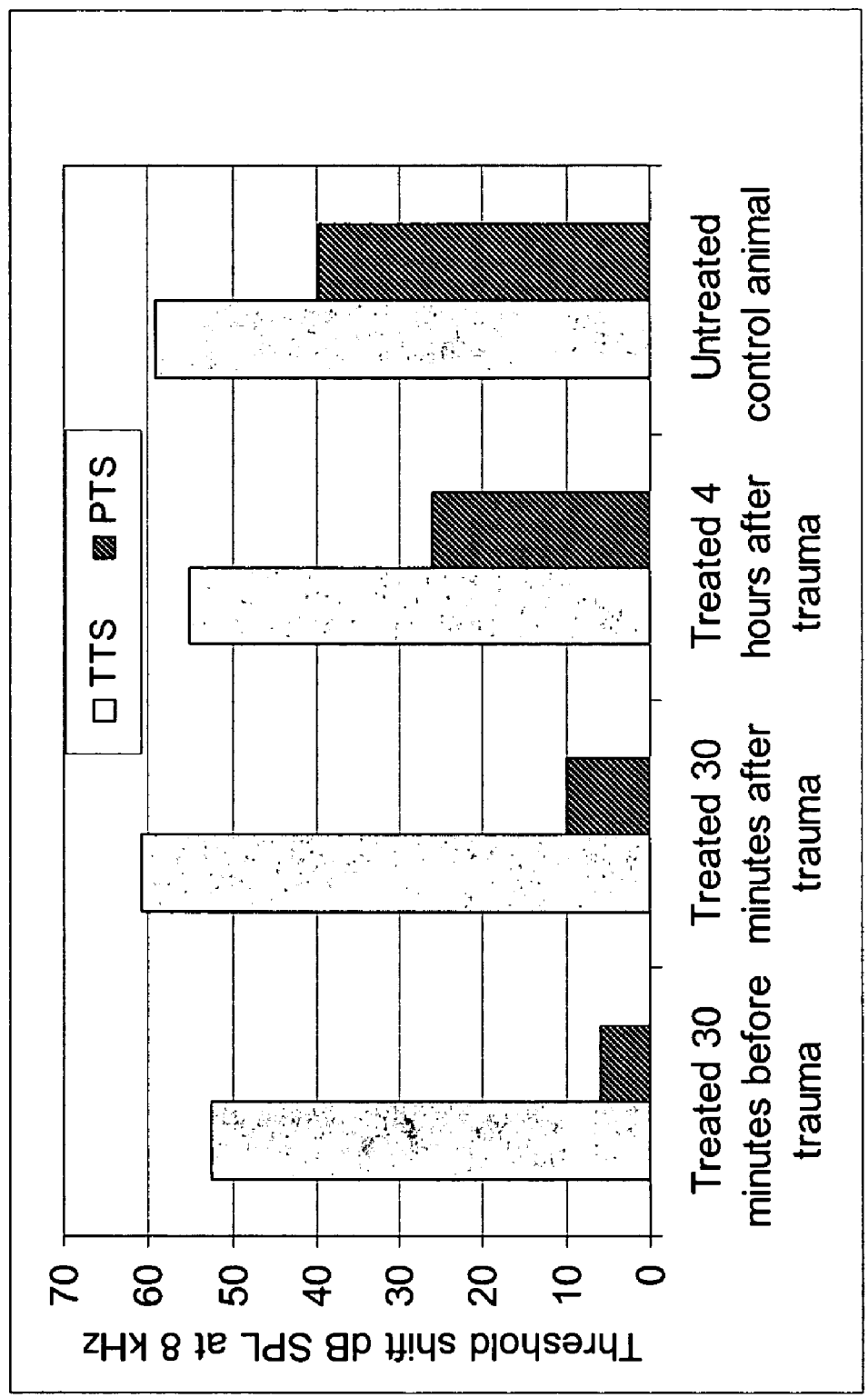
FIG. 7 shows the protecting effect of D-TAT-IB1(s) Protection against permanent hearing loss. Changes of the hearing threshold level (dB sound pressure level) in guinea pigs following noise trauma (120 dB at 6 kHz during 30 minutes) at 8 kHz, the maximally impacted frequency, measured 20 minutes (temporary threshold shift, TTS, grey) and 15 days post noise exposure (permanent threshold shift). Guinea pigs received D-TAT-IB1(s) in a hyaluronic acid gel deposited onto the cochlear round window membrane either 30 minutes before, 30 minutes after or 4 hours after noise trauma; untreated ears served as control. TTS was measured 20 minutes post noise trauma, while PTS (black), which corresponds to permanent hearing loss, was determined after 15 days. As shown, D-TAT-IB1(s) not only protects substantially against permanent hearing loss from noise trauma if applied preventively before the noise exposure, but also in a time-dependent fashion if administered after trauma. PTS in but also in a time-dependent fashion if administered after trauma. PTS in treated ears was significantly lower for administration of D-TAT-IB1(s) 30 minutes and 4 hours post trauma than in untreated control ears.

FIG. 7 shows the protecting effect of D-TAT-IB1(s) Protection against permanent hearing loss. Changes of the hearing threshold level (dB sound pressure level) in guinea pigs following noise trauma (120 dB at 6 kHz during 30 minutes) at 8 kHz, the maximally impacted frequency, measured 20 minutes (temporary threshold shift, TTS, grey) and 15 days post noise exposure (permanent threshold shift). Guinea pigs received D-TAT-IB1(s) in a hyaluronic acid gel deposited onto the cochlear round window membrane either 30 minutes before, 30 minutes after or 4 hours after noise trauma; untreated ears served as control. TTS was measured 20 minutes post noise trauma, while PTS (black), which corresponds to permanent hearing loss, was determined after 15 days. As shown, D-TAT-IB1(s) not only protects substantially against permanent hearing loss from noise trauma if applied preventively before the noise exposure, but also in a time-dependent fashion if administered after trauma. PTS in treated ears was significantly lower for administration of D-TAT-IB1(s) 30 minutes and 4 hours post trauma than in untreated control ears.

EXAMPLES

Example 1

Identification of JNK Inhibitor Sequences

Amino acid sequences important for efficient interaction with JNK were identified by sequence alignments between known JBDs. A sequence comparison between the JBDs of IB1 [SEQ ID NO: 13], IB2 [SEQ ID NO: 14], c-Jun [SEQ ID NO: 15] and ATF2 [SEQ ID NO: 16] defined a weakly conserved 8 amino acid sequence (FIG. 1A). Since the JBDs of IB1 and IB2 are approximately 100 fold as efficient as c-Jun or ATF2 in binding JNK (Dickens et al. Science 277: 693 (1997), it was reasoned that conserved residues between IB1 and IB2 must be important to confer maximal binding. The comparison between the JBDs of IB1 and IB2 defined two blocks of seven and three amino acids that are highly conserved between the two sequences.

These two blocks are contained within a peptide sequence of 19 amino acids in L-IB1(s) [SEQ ID NO: 1] and are also shown for comparative reasons in a 23 aa peptide sequence derived from IB1[SEQ ID NO: 17]. These sequences are shown in FIG. 1B, dashes in the L-IB1 sequence indicate a gap in the sequence in order to align the conserved residues with L-IB1(s).

Example 2

Preparation of JNK Inhibitor Fusion Proteins

Inventive JNK inhibitor fusion proteins according to SEQ ID NO: 9 were synthesized by covalently linking the C-terminal end of SEQ ID NO: 1 to a N-terminal 10 amino acid long carrier peptide derived from the HIV-TAT4g 57 (Vives et al., J Biol. Chem. 272: 16010 (1997)) according to SEQ ID NO: 5 via a linker consisting of two proline residues. This linker was used to allow for maximal flexibility and prevent unwanted secondary structural changes. The basic constructs were also prepared and designated L-IB1(s) (SEQ ID NO: 1) and L-TAT [SEQ ID NO: 5], respectively.

All-D retro-inverso peptides according to SEQ ID NO: 11 were synthesized accordingly. The basic constructs were also prepared and designated D-IB1(s) [SEQ ID NO: 2] and D-TAT [SEQ ID NO: 6], respectively.

All inventive D and L fusion peptides according to SEQ ID NOs: 9, 10, 11 and 12 were produced by classical Fmock synthesis and further analysed by Mass Spectrometry. They were finally purified by HPLC. To determine the effects of the proline linker, two types of TAT peptide were produced one with and one without two prolines. The addition of the two prolines did not appear to modify the entry or the localization of the TAT peptide inside cells. Generic peptides showing the conserved amino acid residues are given in FIG. 2.

Example 3

Inhibition of Cell Death By JBD19

Effects of the 19 aa long JBD sequence of IB1(s) on JNK biological activities were studied. The 19 aa sequence was linked N-terminal to the Green Fluorescent Protein (GFP JBD19 construct), and the effect of this construct on pancreatic β-cell apoptosis induced by IL1 was evaluated. This mode of apoptosis was previously shown to be blocked by transfection with JBD$_{1-280}$ whereas specific inhibitors of ERK1/2 or p38 did not protect (see Ammendrup et al., supra).

Oligonucleotides corresponding to JBD19 and comprising a conserved sequence of 19 amino acids as well as a sequence mutated at the fully conserved regions were synthesized and directionally inserted into the EcoRI and SalI sites of the pEGFP-N1 vector encoding the Green Fluorescent Protein (GFP) (from Clontech). Insulin producing βTC-3 cells were cultured in RPMI 1640 medium supplemented with 10% Fetal Calf Serum, 100 µg/mL Streptomycin, 100 units/mL Penicillin and 2 mM Glutamine. Insulin producing βTC-3 cells were transfected with the indicated vectors and IL-1β (10 ng/mL) was added to the cell culture medium. The number of apoptotic cells was counted at 48 hours after the addition of IL-1β using an inverted fluorescence microscope. Apoptotic cells were discriminated from normal cells by the characteristic "blebbing out" of the cytoplasm and were counted after two days.

GFP is Green Fluorescent protein expression vector used as a control; JBD19 is the vector expressing a chimeric GFP linked to the 19 aa sequence derived from the JBD of IB1; JBD19Mut is the same vector as GFP-JBD19, but with a JBD mutated at four conserved residues shown as FIG. 1B; and $JBD_{1-280}$ is the GFP vector linked to the entire JBD (aa 1-280). The GFP-JBD19 expressing construct prevented IL-1β induced pancreatic β-cell apoptosis as efficiently as the entire $JBD_{1-280}$.

As additional controls, sequences mutated at fully conserved IB1(s) residues had greatly decreased ability to prevent apoptosis.

Example 4

Cellular Import of TAT-IB1(s) Peptides

The ability of the L- and D-enantiomeric forms of TAT and inventive TAT-IB1(s) peptides ("TAT-IB peptides") to enter cells was evaluated. L-TAT, D-TAT, inventive L-TAT-IB1(s), and inventive D-TAT-IB1(s) peptides [SEQ ID NOs: 5, 6, 9 and 12, respectively] were labeled by N-terminal addition of a glycine residue conjugated to fluorescein. Labeled peptides (1 µM) were added to βTC-3 cell cultures, which were maintained as described in Example 3. At predetermined times cells were washed with PBS and fixed for five minutes in ice-cold methanol-acetone (1:1) before being examined under a fluorescence microscope. Fluorescein-labeled BSA (1 µM, 12 moles/mole BSA) was used as a control. Results demonstrated that all the above fluorescein labeled peptides had efficiently and rapidly (less than five minutes) entered cells once added to the culture medium. Conversely, fluorescein labeled bovine serum albumin (1 µM BSA, 12 moles fluorescein/mole BSA) did not enter the cells.

A time course study indicated that the intensity of the fluorescent signal for the L-enantiomeric peptides decreased by 70% following a 24 hours period. Little to no signal was present at 48 hours. In contrast, D-TAT and inventive D-TAT-IB1(s) were extremely stable inside the cells.

Fluorescent signals from these all-D retro-inverso peptides were still very strong 1 week later, and the signal was only slightly diminished at 2 weeks post treatment.

Example 5

In Vitro Inhibition of c-JUN, ATF2 and Elk1 Phosphorylation

The effects of the peptides on JNKs-mediated phosphorylation of their target transcription factors were investigated in vitro. Recombinant and non activated JNK1, JNK2 and JNK3 were produced using a TRANSCRIPTION AND TRANSLATION rabbit reticulocyte lysate kit (Promega) and used in solid phase kinase assays with c-Jun, ATF2 and Elk1, either alone or fused to glutathione-S-transferase (GST), as substrates. Dose response studies were performed wherein inventive L-TAT or L-TAT-IB1(s) peptides (0-25 µM) were mixed with the recombinant JNK1, JNK2, or JNK3 kinases in reaction buffer (20 mM Tris-acetate, 1 mM EGTA, 10 mM p-nitrophenyl-phosphate (pNPP), 5 mM sodium pyrophosphate, 10 mM p-glycerophosphate, 1 mM dithiothreitol) for 20 minutes. The kinase reactions were then initiated by the addition of 10 mM $MgCl_2$ and 5 pCi $^{33}$P-γ-dATP and 1 µg of either GST-Jun (aa 1-89), GST-AFT2 (aa 1-96) or GST-ELK1 (aa 307-428). GST-fusion proteins were purchased from Stratagene (La Jolla, Calif.).

Ten µL of glutathione-agarose beads were also added to the mixture. Reaction products were then separated by SDS-PAGE on a denaturing 10% polyacrylamide gel. Gels were dried and subsequently exposed to X-ray films (Kodak). Nearly complete inhibition of c-Jun, ATF2 and Elk1 phosphorylation by JNKs was observed at inventive TAT-IB(s) peptide doses as low as 2.5 µM. However, a marked exception was the absence of TAT-IB(s) inhibition of JNKS phosphorylation of Elk1. Overall, the inventive TAT-IB1(s) peptide showed superior effects in inhibiting JNK family phosphorylation of their target transcription factors. The ability of D-TAT, inventive D-TAT-IB1(s) and inventive L-TAT-IB1(s) peptides (0-250 µM dosage study) to inhibit GST-Jun (aa 1-73) phosphorylation by recombinant JNK1, JNK2, and JNKS by were analyzed as described above. Overall, D-TAT-IB1(s) peptide decreased JNK-mediated phosphorylation of c-Jun, but at levels approximately 10-20 fold less efficiently than L-TAT-IB1(s).

Example 6

Inhibition of c-JUN Phosphorylation By Activated JNKs

The effects of the L-TAT or inventive L-TAT-IB1(s) peptides on JNKs activated by stressful stimuli were evaluated using GST-Jun to pull down JNKs from UV-light irradiated HeLa cells or IL-1 β treated PTC cells. PTC cells were cultured as described above. HeLa cells were cultured in DMEM medium supplemented with 10% Fetal Calf Serum, 100 µg/mL Streptomycin, 100 units/ml Penicillin and 2 mM Glutamine. One hour prior to being used for cell extract preparation, PTC cells were activated with IL-1 β as described above, whereas HeLa cells were activated by UV-light (20 J/m$^2$). Cell extracts were prepared from control, UV-light irradiated HeLa cells and IL-1β treated βTC-3 cells by scraping the cell cultures in lysis buffer (20 mM Tris-acetate, 1 mM EGTA, 1% Triton X-100, 10 mM p-nitrophenyl-phosphate, 5 mM sodium pyrophosphate, 10 mMP-glycerophosphate, 1 mM dithiothreitol). Debris was removed by centrifugation for five minutes at 15,000 rpm in an SS-34 Beckman rotor. One-hundred µg extracts were incubated for one hour at room temperature with one µg GST-jun (amino acids 1-89) and 10 µL of glutathione-agarose beads (Sigma). Following four washes with the scraping buffer, the beads were resuspended in the same buffer supplemented with L-TAT or inventive L-TAT-IB1(s) peptides (25 µM) for 20 minutes. Kinase reactions were then initiated by addition of 10 mM $MgCl_2$ and 5 pCi $^{33}$P-γ-dATP and incubated for 30 minutes at 30° C.

Reaction products were then separated by SDS-PAGE on a denaturing 10% polyacrylamide gel. Gels were dried and subsequently exposed to X-ray films (Kodak). The inventive TAT-IB(s) peptides efficiently prevented phosphorylation of c-Jun by activated JNKs in these experiments.

Example 7

In Vivo Inhibition of c-JUN Phosphorylation by Inventive TAT-IB(s) Peptides

To determine whether the inventive cell-permeable peptides could block JNK signaling in vivo, we used a heterologous GAL4 system. HeLa cells, cultured as described above, were co-transfected with the 5×GAL-LUC reporter vector together with the GAL-Jun expression construct (Stratagene) comprising the activation domain of c-Jun (amino acids 1-89) linked to the GAL4 DNA-binding domain. Activation of JNK was achieved by the co-transfection of vectors expressing the directly upstream kinases MKK4 and MKK7 (see Whitmarsh et al., Science 285: 1578 (1999)). Briefly, $3 \times 10^5$ cells were transfected with the plasmids in 3.5-cm dishes using DOTAP (Boehringer Mannheim) following instructions from the manufacturer. For experiments involving GAL-Jun, 20 ng of the plasmid was transfected with 1 µg of the reporter plasmid pFR-Luc (Stratagene) and 0.5 µg of either MKK4 or MKK7 expressing plasmids. Three hours following transfection, cell media were changed and TAT and TAT-IB1(s) peptides (1 µM) were added. The luciferase activities were measured 16 hours later using the "Dual Reporter System" from Promega after normalization to protein content. Addition of TAT-IB1(s) peptide blocked activation of c-Jun following MKK4 and MKK7 mediated activation of JNK. Because HeLa cells express JNK1 and JNK2 isoforms but not JNK3, we transfected cells with JNK3. Again, the TAT-IB(s) peptide inhibited JNK2 mediated activation of c-Jun.

Example 8

Inhibition of IL-1β Induced Pancreatic β-Cell Death by TAT-IB Peptides

We investigated the effects of the inventive L-TAT-IB(s) peptides on the promotion of β-cell apoptosis elicited by IL-1. βTC-3 cell cultures were incubated for 30 minutes with 1 µM of inventive L-TAT-IB1(s) peptides followed by 10 ng/mL of IL-1. A second addition of peptide (1 µM) was performed 24 hours later. Apoptotic cells were counted after two days of incubation with IL-1 β using propidium iodide (red stained cell are dead cells) and Hoechst 33342 (blue stained cell are cells with intact plasma membrane) nuclear staining. Addition of the inventive TAT-IB(s) peptides inhibited IL-1-induced apoptosis of βTC-3 cells cultured in the presence of IL-1 β for two days.

Long term inhibition of IL-1 induced cells death was examined by treating βTC-3 cells as described above, except that incubation of the cells with the peptides and IL-1 β was sustained for 12 days. Additional peptides (1 µM) were added each day and additional IL-1 β (10 ng/mL) was added every 2 days. The inventive TAT-IB1(s) peptide confers strong protection against apoptosis in these conditions. Taken together, these experiments provide evidence that inventive TAT-IB(s) peptides are biologically active molecules able to prevent the effects of JNK signaling on cell fate.

Example 9

Synthesis of Inventive All-D Retro-Inverso IB(s) Peptides

Peptides of the invention may be all-D amino acid peptides synthesized in reverse to prevent natural proteolysis (i.e. all-D retro-inverso peptides). An all-D retro-inverso peptide of the invention would provide a peptide with functional properties similar to the native peptide, wherein the side groups of the component amino acids would correspond to the native peptide alignment, but would retain a protease resistant backbone.

Retro-inverso peptides of the invention are analogs synthesized using D-amino acids by attaching the amino acids in a peptide chain such that the sequence of amino acids in the retro-inverso peptide analog is exactly opposite of that in the selected peptide which serves as the model. To illustrate, if the naturally occurring TAT protein (formed of L-amino acids) has the sequence GRKKRRQRRR [SEQ ID NO: 5], the retro-inverso peptide analog of this peptide (formed of D-amino acids) would have the sequence RRRQRRKKRG [SEQ ID NO: 6]. The procedures for synthesizing a chain of D-amino acids to form the retro-inverso peptides are known in the art (see e.g. Jameson et al., Nature, 368, 744-746 (1994); Brady et al., Nature, 368, 692-693 (1994); Guichard et al., J. Med. Chem. 39, 2030-2039 (1996)). Specifically, the retro-peptides were produced by classical F-mock synthesis and further analyzed by Mass Spectrometry. They were finally purified by HPLC.

Since an inherent problem with native peptides is degradation by natural proteases and inherent immunogenicity, the heterobivalent or heteromultivalent compounds of this invention will be prepared to include the "retro-inverso isomer" of the desired peptide. Protecting the peptide from natural proteolysis should therefore increase the effectiveness of the specific heterobivalent or heteromultivalent compound, both by prolonging half-life and decreasing the extent of the immune response aimed at actively destroying the peptides.

Example 10

Long Term Biological Activity of Inventive All-D Retro-Inverso IB(s) Peptides

Long term biological activity is predicted for the inventive D-TAT-IB(s) retro-inverso containing peptide heteroconjugate when compared to the native L-amino acid analog owing to protection of the inventive D-TAT-IB(s) peptide from degradation by native proteases, as shown in Example 5.

Inhibition of IL-1 β induced pancreatic β-cell death by the inventive D-TAT-IB1(s) peptide was analyzed. βTC-3 cells were incubated as described above for 30 minutes with one single addition of the indicated peptides (1, µM), then IL-1 (10 ng/ml) was added.

Apoptotic cells were then counted after two days of incubation with IL-1 β by use of Propidium Iodide and Hoechst 33342 nuclear staining. A minimum of 1,000 cells were counted for each experiment. Standard Error of the Means (SEM) are indicated, n=5. The D-TAT-IB1 peptide decreased IL-1 induced apoptosis to a similar extent as L-TAT-IB peptides.

Long term inhibition of IL-1P induced cell-death by the D-TAT-IB1 peptide was also analyzed. βTC-3 cells were incubated as above for 30 minutes with one single addition of the indicated peptides (1 µM), then IL-1 β (10 ng/ml) was added, followed by addition of the cytokine every two days. Apoptotic cells were then counted after 15 days of incubation with IL-1 by use of propidium iodide and Hoechst 33342 nuclear staining. Note that one single addition of the TAT-IB 1 peptide does not confer long-term protection. A minimum of 1.000 cells were counted for each experiment. As a result, inventive D-TAT-IB1 (s), but not inventive L-TAT-IB1 (s), was able to confer long term (15 day) protection.

Example 11

Inhibition of Irradiation Induced Pancreatic β-Cell Death by TAT-IB(s) Peptides

JNK is also activated by ionizing radiation. To determine whether inventive TAT-IB(s) peptides would provide protection against radiation-induced JNK damage, "WiDr" cells were irradiated (30 Gy) in presence or absence of D-TAT, inventive L-TAT-IB1(s) or inventive D-TAT-IB1(s) peptides (1 μM added 30 minutes before irradiation). Control cells (CTRL) were not irradiated. Cells were analyzed 48 hours later by means of PI and Hoechst 3342 staining, as described above. N=3, SEM are indicated. Inventive L-TAT-IB1(s) and D-TAT-IB1(s) peptides were both able to prevent irradiation induced apoptosis in this human colon cancer line.

Example 12

Radioprotection to Ionizing Radiation by Inventive TAT-IB(s) Peptides

To determine the radioprotective effects of the inventive TAT-IB(s) peptides, C57B1/6 mice (2 to 3 months old) were irradiated with a Phillips RT 250 R-ray at a dose rate of 0.74 Gy/min (17 mA, 0.5 mm Cu filter). Thirty minutes prior to irradiation, the animals were injected i.p. with either TAT, inventive L-TAT-IB1(s) or inventive D-TAT-IB1(s) peptides (30l of a 1 mM solution). Briefly, mice were irradiated as follows: mice were placed in small plastic boxes with the head lying outside the box. The animals were placed on their back under the irradiator, and their neck fixed in a small plastic tunnel to maintain their head in a correct position. The body was protected with lead.

Prior to irradiation mice were maintained on standard pellet mouse chow, however post irradiation mice were fed with a semi-liquid food that was renewed each day.

The reaction of the lip mucosa was then scored by 2 independent observers according to the scoring system developed by Parkins et al. (Parkins et al, Radiotherapy & Oncology, 1: 165-173, 1983), in which the erythema status as well as the presence of edema, desquamation and exudation was quoted. Additionally, animals were weighed before each recording of their erythema/edema status.

The results of these experiments indicate that the inventive TAT-IB(s) peptides can protect against weight loss and erythema/edema associated with ionizing radiation.

Example 13

Suppression of JNK Transcription Factors by Inventive L-TAT-IB1(s) Peptides

Gel retardation assays were carried out with an AP-1 doubled labeled probe (5'-CGC TTG ATG AGT CAG CCG GAA-3' (SEQ ID NO: 27). HeLa cell nuclear extracts that were treated or not for one hour with 5 ng/mlTNF-α, as indicated. TAT and inventive L-TAT-IB1(s) peptides were added 30 minutes before TNF-α. Only the part of the gel with the specific AP-1 DNA complex (as demonstrated by competition experiments with non-labeled specific and non-specific competitors) is shown.

Inventive L-TAT-IB1(s) peptides decrease the formation of the AP-1 DNA binding complex in the presence of TNF-α.

Example 14

Evaluation of the Neuroprotection Against Focal Cerebral Ischemia, in a Permanent MCAO Model-Determination of the Efficacity of the Protection at Different Doses. (see FIG. 3)

Focal cerebral ischemia was induced in 12-days-old rats. Pups were anesthetized in an induction chamber with 2% isoflurane and during the operation anaesthesia was maintained using a mask under 2% isoflurane. MCAO was induced by electrocoagulating a main branch of the middle cerebral artery (MCA). Rats were placed on the right side, and an oblique dermal incision was made between the ear and eye. After excision of the temporal muscle, the cranial bone was removed from the frontal suture to a level below the zygomatic arch. The left MCA, exposed just after its apparition over the rhinal fissure, was permanently electrocoagulated at the inferior cerebral vein level before the MCA bifurcated into frontal and parietal branches. The cranial skin incision was then closed. Rat pups were then placed in an incubator maintained at 37° C. until they awoke, and were then transferred to their mother.

6 hours later an inventive chimeric D-TAT-IB1(s) peptide according to SEQ ID NO: 11 was injected intraperitoneally. 24 hours after the coagulation, the rats were anesthetized with chloral hydrate and perfused through the ascending aorta with 4% paraformaldehyde in PBS. Brains were then removed and kept for 2 hours in the same fixative solution, and placed in a gradient of 30% sucrose in PBS for about 15 hours at 4° C. Brains were frozen in isopentane (−40° C.) and stored at −20° C. Coronal cryostat sections of 50 □m were collected on glass slides. The sections were stained with cresyl violet. Each tenth section was analyzed and the total volume of the lesion was calculated using the Neuroleucida programme. In the control group A, the mean lesion volume was 21.47 mm³. All the treated groups have a lower mean than the control group. A significant statistic difference is observed between group A and groups C, E and F (one-tailed t-test, p=0.030, p=0.002, p=0.001 respectively). The results are shown in FIG. 4.

As a result, these data support the conclusion that the inventive chimeric D-TAT-IB1(s) peptide according to SEQ ID NO: 11, administered at a dose of 11 mg/kg, 3 mg/kg, 0.3 mg/kg and 0.03 mg/kg, contributes to a cerebral protection. Results at a dose of 1 mg/kg, 0.003 mg/kg and 0.0003 compared to saline group suggest that the total sample was not large enough to reach a significant difference. The best protection is observed at the dose of 0.03 mg/kg.

Example 15

Evaluation of neuroprotection by inventive chimeric peptides after iv administration against focal cerebral ischaemia, in a transient MCAO model (see FIG. 4).

Transient ischemia in adult mice. Using male ICR-CD1 mice (6 weeks old; 18-37 g; Harlan), we provoked ischemia by introducing a filament from the common carotid artery into the internal carotid and advancing it into the arterial circle, thereby occluding the middle cerebral artery. We measured regional cerebral blood flow by laser Doppler flowmetry, with a probe fixed on the skull throughout the ischemia until 10 min after reperfusion. Rectal temperature was measured and maintained at 37° C. The mice were killed 48 h after reperfusion. Serial cryostat sections 20 μm thick were traced using a computer-microscope system equipped with the Neurolucida program (MicroBrightField) and the volumes of the ischemic area and of the whole brain were calculated (blinded) with the Neuroexplorer program.

XG–102 0.3=0.3 mg/kg,XG–102 1=1 mg/kg, XG–102 5=5 mg/kg

The infarct volume sizes (mm$^3$) after bolus iv administration of placebo and XG-102 0.3, 1.3 mg/kg 6 hours after reperfusion (30 minutes clamp) in an adult mice model were as follows.

| infarcts | moyenne | écart type |
|---|---|---|
| control n = 5 | 72 | 17 |
| XG102 0.3 n = 5 | 16 | 4 |
| XG102 1 n = 1 | 16 | |
| XG102 3 n = 5 | 15 | 5 |

Example 16

Assay on Neuronal Cultures by Measuring LDH Release Following NMDA Stimulation (see FIG. 5)

The neuroprotective effect of the D-TAT-IB (generic)(s)/D-JNKI1 peptide (SEQ ID NO: 12) was evaluated in sister cultures pre-treated for 30 min with the indicated concentrations of peptides or MK-801 before continuous exposure to 100 μM NMDA. After 12 h of NMDA treatment, in cultures pretreated with 5 μM of D-TAT-IB (generic)(s)/D-JNKI1 the degenerative changes due to NMDA exposure were completely inhibited as indicated by the absence of significant LDH release above controls (FIG. 5). The morphological appearance, number and distribution of the neurons were indistinguishable from the controls.

Cortical neuronal culture. We dissected small pieces of cortex from the brains of two day old rat pups, incubated them with 200 units of papain for 30 min at 34° C., and then plated the neurons at densities of approximately 1×10$^6$ cells/plate on dishes pre-coated with 100 μg/ml poly-D-lysine. The plating medium consisted of B27/Neurobasal (Life Technologies, Gaithersburg, Md.) supplemented with 0.5 mM glutamine, 100 U/ml penicillin and 100 ug/ml streptomycin.

Lactate dehydrogenate (LDH) cytotoxicity assay. LDH released into the bathing medium 12, 24 and 48 h after NMDA administration was measured using the Cytotox 96 non-radioactive cytotoxicity assay kit (Promega, Wis.) (see FIG. 5).

Example 17

Inhibition of Endogenous JNK Activity in HepG2 Cells Using an All-In One Well Approach (see FIG. 6)

HepG2 cells were seeded at 3,000 cells/well the day prior the experiment. Then, increasing concentrations of either interleukin-1β [IL-1β(■)] or tumor necrosis factor α[TNFα (●)] (a) were added to activate JNK for 30 minutes. Cells were lysed in 20 mM Hepes, 0.5% Tween pH 7.4 and processed for AlphaScreen JNK. (b) Z' for the JNK activity induced by 10 ng/ml IL-1β and measured in 384 wells/plate (n=96). (c) Inhibition of endogenous IL-1β-induced JNK activity with chemical JNK inhibitors [staurosporin (○) and SP600125 (●)]. (d) Effect of peptidic inhibitors L-TAT-IB1(s) according to SEQ ID NO: 9 [here abbreviated as L-JNKi (■)) and D-TAT-IB1(s) according to SEQ ID NO: 11 (here abbreviated as D-JNKi (□)) and JBDs (●) (corresponds to L-JNKI without the TAT sequence)] on IL-1α dependent JNK activity. All panels are representative of three independent experiments (n=3).

Methods: Alphascreen Kinase Assay

Principle: AlphaScreen is a non-radioactive bead-based technology used to study biomolecular interactions in a microplate format. The acronym ALPHA stands for Amplified Luminescence Proximity Homogenous Assay. It involves a biological interaction that brings a "donor" and an "acceptor" beads in close proximity, then a cascade of chemical reactions acts to produce an amplified signal. Upon laser excitation at 680 nm, a photosensitizer (phthalocyanine) in the "donor" bead converts ambient oxygen to an excited singlet state. Within its 4 μsec half-life, the singlet oxygen molecule can diffuse up to approximately 200 nm in solution and if an acceptor bead is within that proximity, the singlet oxygen reacts with a thioxene derivative in the "acceptor" bead, generating chemiluminescence at 370 nm that further activates fluorophores contained in the same "acceptor" bead. The excited fluorophores subsequently emit light at 520-620 nm. In the absence of an acceptor bead, singlet oxygen falls to ground state and no signal is produced.

Kinase reagents (B-GST-cJun, anti P-cJun antibody and active JNKS) were first diluted in kinase buffer (20 mM Tris-HCl pH 7.6, 10 mM MgCl$_2$, 1 mM DTT, 100 μM Na$_3$VO$_4$, 0.01% Tween-20) and added to wells (15 μl). Reactions were then incubated in presence of 10 μM of ATP for 1 h at 23° C. Detection was performed by an addition of 10 μl of beads mix (Protein A acceptor 20 μg/ml and Streptavidin donor 20 μg/ml), diluted in detection buffer (20 mM Tris-HCl pH 7.4, 20 mM NaCl, 80 mM EDTA, 0.3% BSA), followed by an another one-hour incubation at 23° C. in the dark. For measurement of JNK endogenous activity, kinase assays were performed as described above except active JNK3 was replaced by cells lysates and reaction kinase components were added after the cells lysis. B-GST-cjun and P-cJun antibody were used at the same concentrations whereas ATP was used at 50 μM instead of 10 μM. AlphaScreen signal was analyzed directly on the Fusion or En Vision apparatus.

Example 18

Treatment of Noise Trauma

D-TAT-IB1(s) was applied onto the round window membrane of the cochlea of 3 groups of guinea pigs (each group with 6 animals) in 2 microliters of a gel formulation of 2.6% buffered hyaluronic acid (Hylumed, Genzyme Corp.) at a concentration of 100 □M either 30 minutes before noise trauma (120 dB at 6 kHz during 30 minutes) or 30 minutes or 4 hours thereafter. Untreated ears served as control. Hearing threshold shifts were evaluated by auditory brainstem response measurements 20 minutes after noise trauma (temporary threshold shift, TTS) and 15 days following the trauma (permanent threshold shift, PTS). Administration of D-TAT-IB1(s) protected against permanent hearing loss even if applied after exposure to excessive noise compared to nontreated ears. The protective effect was stronger the earlier D-TAT-IB1(s) was administered after the noise trauma. Thus, D-TAT-IB1 (s) is a very effective otoprotective compound in case of noise trauma.

From the foregoing detailed description of the specific embodiments of the invention, it should be apparent that unique cell-permeable bioactive chimeric peptides and JNK inhibitor sequences have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

The invention claimed is:

1. A c-Jun amino terminal kinase (JNK) binding peptide, wherein the binding peptide consists of the amino acid sequence of SEQ ID NO:11, wherein all of the amino acids of the binding peptide are in the D isomer form, and wherein the binding peptide is capable of inhibiting JNK kinase activity when the binding peptide is present in a JNK expressing cell.

2. The JNK binding peptide of claim 1, wherein the JNK binding peptide inhibits the activation of at least one JNK targeted transcription factor when the JNK binding peptide is present in a JNK expressing cell.

3. The JNK binding peptide of claim 2, wherein the JNK targeted transcription factor is selected from the group consisting of c-Jun, ATF2, and Elk.

4. A pharmaceutical composition comprising the JNK binding peptide of claim 1, and a pharmaceutically acceptable carrier.

5. The pharmaceutical composition of claim 4, wherein the pharmaceutical composition is to be administered by an administration route selected from the group consisting of intraperitoneal, nasal, intravenous, oral and patch delivery.

6. A kit comprising the JNK binding peptide according to claim 1.

* * * * *

```
                         SEQUENCE LISTING

<160> NUMBER OF SEQ ID NOS: 27

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: chemically
      synthesized

<400> SEQUENCE: 1

Arg Pro Lys Arg Pro Thr Thr Leu Asn Leu Phe Pro Gln Val Pro Arg
1               5                   10                  15

Ser Gln Asp

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: chemically
      synthesized

<400> SEQUENCE: 2

Asp Gln Ser Arg Pro Val Gln Pro Phe Leu Asn Leu Thr Thr Pro Arg
1               5                   10                  15

Lys Pro Arg

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: Xaa represents any amino acid except Serine or
      Threonine
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 3

Xaa Xaa Arg Pro Thr Thr Leu Xaa Leu Xaa Xaa Xaa Xaa Xaa Xaa Xaa
1               5                   10                  15

Gln Asp Xaa
```

```
<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: chemically
      synthesized
<220> FEATURE:
<221> NAME/KEY: MISC_FEATURE
<222> LOCATION: (1)..(1)
<223> OTHER INFORMATION: Xaa represents any D or L amino acid
<220> FEATURE:
<221> NAME/KEY: misc_feature
<222> LOCATION: (4)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: Xaa represents any D or L amino acid
<220> FEATURE:
<221> NAME/KEY: MISC_FEATURE
<222> LOCATION: (19)..(19)
<223> OTHER INFORMATION: Xaa represents any D or L amino acid

<400> SEQUENCE: 4

Xaa Asp Gln Xaa Xaa Xaa Xaa Xaa Xaa Xaa Leu Xaa Leu Thr Thr Pro
1               5                   10                  15

Arg Xaa Xaa

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: chemically
      synthesized

<400> SEQUENCE: 5

Gly Arg Lys Lys Arg Arg Gln Arg Arg Arg
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: chemically
      synthesized

<400> SEQUENCE: 6

Arg Arg Arg Gln Arg Arg Lys Lys Arg Gly
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: chemically
      synthesized
<220> FEATURE:
<221> NAME/KEY: MISC_FEATURE
<222> LOCATION: (1)..(1)
<223> OTHER INFORMATION: Xaa represents any D or L amino acid
<220> FEATURE:
<221> NAME/KEY: MISC_FEATURE
<222> LOCATION: (11)..(11)
<223> OTHER INFORMATION: Xaa represents any D or L amino acid
```

```
<400> SEQUENCE: 7

Xaa Arg Lys Lys Arg Arg Gln Arg Arg Xaa
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: chemically
      synthesized
<220> FEATURE:
<221> NAME/KEY: MISC_FEATURE
<222> LOCATION: (1)..(1)
<223> OTHER INFORMATION: Xaa represents any D or L amino acid
<220> FEATURE:
<221> NAME/KEY: MISC_FEATURE
<222> LOCATION: (11)..(11)
<223> OTHER INFORMATION: Xaa represents any D or L amino acid

<400> SEQUENCE: 8

Xaa Arg Arg Arg Gln Arg Arg Lys Lys Arg Xaa
1               5                   10

<210> SEQ ID NO 9
<211> LENGTH: 31
<212> TYPE: PRT
<213> ORGANISM: Artificial Sequence
<220> FEATURE:
<223> OTHER INFORMATION: Description of Artificial Sequence: chemically
      synthesized

<400> SEQUENCE: 9

Gly Arg Lys Lys Arg Arg Gln Arg Arg Arg Pro Pro Arg Pro Lys Arg
1               5                   10                  15

Pro Thr Thr Leu Asn Leu Phe Pro Gln Val Pro Arg Ser Gln Asp
            20                  25                  30

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: chemically
      synthesized
<220> FEATURE:
<221> NAME/KEY: MISC_FEATURE
<222> LOCATION: (1)..(1)
<223> OTHER INFORMATION: Xaa represents any D or L amino acid.
<220> FEATURE:
<221> NAME/KEY: MISC_FEATURE
<222> LOCATION: (11)..(11)
<223> OTHER INFORMATION: Xaa represents any D or L amino acid.
<220> FEATURE:
<221> NAME/KEY: MISC_FEATURE
<222> LOCATION: (12)..(12)
<223> OTHER INFORMATION: Xaa represents any D or L amino acid.
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(26)
<223> OTHER INFORMATION: Xaa can be any naturally occurring amino acid
<220> FEATURE:
<221> NAME/KEY: MISC_FEATURE
<222> LOCATION: (29)..(29)
<223> OTHER INFORMATION: Xaa represents any D or L amino acid.

<400> SEQUENCE: 10
```

Xaa Arg Lys Lys Arg Gln Arg Arg Xaa Xaa Arg Pro Thr Thr
1               5                   10                  15

Leu Xaa Leu Xaa Xaa Xaa Xaa Xaa Xaa Gln Asp Xaa
            20                  25

<210> SEQ ID NO 11
<211> LENGTH: 31
<212> TYPE: PRT
<213> ORGANISM: Artificial Sequence
<220> FEATURE:
<223> OTHER INFORMATION: Description of Artificial Sequence: chemically
      synthesized

<400> SEQUENCE: 11

Asp Gln Ser Arg Pro Val Gln Pro Phe Leu Asn Leu Thr Thr Pro Arg
1               5                   10                  15

Lys Pro Arg Pro Pro Arg Arg Arg Gln Arg Arg Lys Lys Arg Gly
            20                  25                  30

<210> SEQ ID NO 12
<211> LENGTH: 29
<212> TYPE: PRT
<213> ORGANISM: Artificial Sequence
<220> FEATURE:
<223> OTHER INFORMATION: Description of Artificial Sequence: chemically
      synthesized
<220> FEATURE:
<221> NAME/KEY: MISC_FEATURE
<222> LOCATION: (1)..(1)
<223> OTHER INFORMATION: Xaa represents any D or L amino acid
<220> FEATURE:
<221> NAME/KEY: misc_feature
<222> LOCATION: (4)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: Xaa represents any D or L amino acid
<220> FEATURE:
<221> NAME/KEY: MISC_FEATURE
<222> LOCATION: (19)..(19)
<223> OTHER INFORMATION: Xaa represents any D or L amino acid
<220> FEATURE:
<221> NAME/KEY: MISC_FEATURE
<222> LOCATION: (29)..(29)
<223> OTHER INFORMATION: Xaa represents any D or L amino acid

<400> SEQUENCE: 12

Xaa Asp Gln Xaa Xaa Xaa Xaa Xaa Xaa Xaa Leu Xaa Leu Thr Thr Pro
1               5                   10                  15

Arg Xaa Xaa Arg Arg Arg Gln Arg Arg Lys Lys Arg Xaa
            20                  25

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: chemically
      synthesized

<400> SEQUENCE: 13

Pro Gly Thr Gly Cys Gly Asp Thr Tyr Arg Pro Lys Arg Pro Thr Thr
1               5                   10                  15

Leu Asn Leu Phe Pro Gln Val Pro Arg Ser Gln Asp Thr
            20                  25

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence: chemically
      synthesized

<400> SEQUENCE: 14

Ile Pro Ser Pro Ser Val Glu Glu Pro His Lys His Arg Pro Thr Thr
1               5                   10                  15

Leu Arg Leu Thr Thr Leu Gly Ala Gln Asp Ser
            20                  25

<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence: chemically
      synthesized

<400> SEQUENCE: 15

Gly Ala Tyr Gly Tyr Ser Asn Pro Lys Ile Leu Lys Gln Ser Met Thr
1               5                   10                  15

Leu Asn Leu Ala Asp Pro Val Gly Asn Leu Lys Pro His
            20                  25

<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: chemically
      synthesized

<400> SEQUENCE: 16

Thr Asn Glu Asp His Leu Ala Val His Lys His Lys His Glu Met Thr
1               5                   10                  15

Leu Lys Phe Gly Pro Ala Arg Asn Asp Ser Val Ile Val
            20                  25

<210> SEQ ID NO 17
<211> LENGTH: 23
<212> TYPE: PRT
<213> ORGANISM: Artificial Sequence
<220> FEATURE:
<223> OTHER INFORMATION: Description of Artificial Sequence: chemically
      synthesized

<400> SEQUENCE: 17

Asp Thr Tyr Arg Pro Lys Arg Pro Thr Thr Leu Asn Leu Phe Pro Gln
1               5                   10                  15

Val Pro Arg Ser Gln Asp Thr
            20

<210> SEQ ID NO 18
<211> LENGTH: 23
<212> TYPE: PRT
<213> ORGANISM: Artificial Sequence
<220> FEATURE:
<223> OTHER INFORMATION: Description of Artifical Sequence: chemically
      synthesized

<400> SEQUENCE: 18

Thr Asp Gln Ser Arg Pro Val Gln Pro Phe Leu Asn Leu Thr Thr Pro
1               5                  10                 15

Arg Lys Pro Arg Tyr Thr Asp
            20

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(15)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: Xaa represents either Ser or Thr
<220> FEATURE:
<221> NAME/KEY: misc_feature
<222> LOCATION: (19)..(19)
<223> OTHER INFORMATION: Xaa can be any naturally occurring amino acid

<400> SEQUENCE: 19

Xaa Arg Pro Thr Thr Leu Xaa Leu Xaa Xaa Xaa Xaa Xaa Xaa Xaa Gln
1               5                  10                 15

Asp Xaa Xaa

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: Xaa represents either Ser or Thr
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 20

Xaa Xaa Asp Gln Xaa Xaa Xaa Xaa Xaa Xaa Xaa Leu Xaa Leu Thr Thr
1               5                  10                 15

Pro Arg Xaa

<210> SEQ ID NO 21

```
<211> LENGTH: 17
<212> TYPE: PRT
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid

<400> SEQUENCE: 21

Xaa Xaa Xaa Xaa Arg Lys Lys Arg Arg Gln Arg Arg Arg Xaa Xaa Xaa
1               5                   10                  15

Xaa

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid

<400> SEQUENCE: 22

Xaa Xaa Xaa Xaa Arg Arg Arg Gln Arg Arg Lys Lys Arg Xaa Xaa Xaa
1               5                   10                  15

Xaa

<210> SEQ ID NO 23
<211> LENGTH: 35
<212> TYPE: PRT
<213> ORGANISM: Artificial Sequence
<220> FEATURE:
<223> OTHER INFORMATION: Description of Artificial Sequence: chemically
      synthesized

<400> SEQUENCE: 23

Gly Arg Lys Lys Arg Arg Gln Arg Arg Arg Pro Pro Asp Thr Tyr Arg
1               5                   10                  15

Pro Lys Arg Pro Thr Thr Leu Asn Leu Phe Pro Gln Val Pro Arg Ser
            20                  25                  30

Gln Asp Thr
        35

<210> SEQ ID NO 24
<211> LENGTH: 42
<212> TYPE: PRT
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
```

-continued

```
<222> LOCATION: (17)..(24)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (32)..(38)
<223> OTHER INFORMATION: Xaa can be any naturally occurring amino acid
<220> FEATURE:
<221> NAME/KEY: MISC_FEATURE
<222> LOCATION: (41)..(41)
<223> OTHER INFORMATION: Xaa represents either Ser or Thr
<220> FEATURE:
<221> NAME/KEY: misc_feature
<222> LOCATION: (42)..(42)
<223> OTHER INFORMATION: Xaa can be any naturally occurring amino acid

<400> SEQUENCE: 24

Xaa Xaa Xaa Xaa Xaa Xaa Xaa Arg Lys Lys Arg Arg Gln Arg Arg Arg
 1               5                  10                  15

Xaa Xaa Xaa Xaa Xaa Xaa Xaa Xaa Arg Pro Thr Thr Leu Xaa Leu Xaa
            20                  25                  30

Xaa Xaa Xaa Xaa Xaa Xaa Gln Asp Xaa Xaa
        35                  40

<210> SEQ ID NO 25
<211> LENGTH: 35
<212> TYPE: PRT
<213> ORGANISM: Artificial Sequence
<220> FEATURE:
<223> OTHER INFORMATION: Description of Artificial Sequence: chemically
      synthesized

<400> SEQUENCE: 25

Thr Asp Gln Ser Arg Pro Val Gln Pro Phe Leu Asn Leu Thr Thr Pro
 1               5                  10                  15

Arg Lys Pro Arg Tyr Thr Asp Pro Pro Arg Arg Gln Arg Arg Lys
            20                  25                  30

Lys Arg Gly
        35

<210> SEQ ID NO 26
<211> LENGTH: 42
<212> TYPE: PRT
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: Xaa represents either Ser or Thr
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (19)..(26)
<223> OTHER INFORMATION: Xaa can be any naturally occurring amino acid
<220> FEATURE:
<221> NAME/KEY: misc_feature
```

```
<222> LOCATION: (36)..(42)
<223> OTHER INFORMATION: Xaa can be any naturally occurring amino acid

<400> SEQUENCE: 26

Xaa Xaa Asp Gln Xaa Xaa Xaa Xaa Xaa Xaa Xaa Leu Xaa Leu Thr Thr
 1               5                  10                  15

Pro Arg Xaa Xaa Xaa Xaa Xaa Xaa Xaa Arg Arg Arg Gln Arg Arg
            20                  25                  30

Lys Lys Arg Xaa Xaa Xaa Xaa Xaa Xaa Xaa
        35                  40

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 27
cgcttgatga gtcagccgga a                                           21
```